(12) United States Patent
Eden et al.

(10) Patent No.: US 12,423,715 B2
(45) Date of Patent: Sep. 23, 2025

(54) OPTIMIZING ORGANIC GROWTH USING SPECTRAL MEASUREMENT

(71) Applicant: CAN TECHNOLOGIES, INC., Wayzata, MN (US)

(72) Inventors: Eric John Eden, Champlin, MN (US); Richard Joel Faris, Nowthen, MN (US); Delphine Marie Pierre Melchior, Crein (FR)

(73) Assignee: CAN TECHNOLOGIES, INC., Wayzata, MN (US)

( * ) Notice: Subject to any disclaimer, the term of this patent is extended or adjusted under 35 U.S.C. 154(b) by 1026 days.

(21) Appl. No.: 17/273,474

(22) PCT Filed: Sep. 4, 2019

(86) PCT No.: PCT/US2019/049438
§ 371 (c)(1),
(2) Date: Mar. 4, 2021

(87) PCT Pub. No.: WO2020/051176
PCT Pub. Date: Mar. 12, 2020

(65) Prior Publication Data
US 2021/0319460 A1    Oct. 14, 2021

Related U.S. Application Data

(60) Provisional application No. 62/728,332, filed on Sep. 7, 2018.

(51) Int. Cl.
*G06Q 30/02* (2023.01)
*A61B 5/00* (2006.01)
*G06Q 30/0201* (2023.01)

(52) U.S. Cl.
CPC ....... *G06Q 30/0201* (2013.01); *A61B 5/0064* (2013.01); *A61B 5/0075* (2013.01); *A61B 2503/40* (2013.01)

(58) Field of Classification Search
CPC .. G06Q 30/02; G06Q 30/0201; A61B 5/0064; A61B 5/0093; A61B 5/0075; A61B 2503/40; A61B 2017/00057; A61B 2017/00061; A61D 7/00
See application file for complete search history.

(56) References Cited

U.S. PATENT DOCUMENTS

| | | |
|---|---|---|
| 5,576,949 A | 11/1996 | Scofield |
| 6,493,566 B1 | 12/2002 | Ruchti |
| 6,512,937 B2 | 1/2003 | Blank |

(Continued)

FOREIGN PATENT DOCUMENTS

| | | |
|---|---|---|
| CN | 105259131 A | 1/2016 |
| CN | 107664616 A | 2/2018 |

(Continued)

*Primary Examiner* — Oneal R Mistry
*Assistant Examiner* — Duy Tran

(57) ABSTRACT

A system for measuring a market performance metric of an animal comprising: a sensor unit that detects an emitted spectrum from the animal wherein the sensor unit filters the received emitted spectra to a set of spectral values; and a memory unit that comprises a set of predetermined chemometric data correlated to at least the market performance metric, wherein the memory unit is correlated to the set of spectral values.

28 Claims, 15 Drawing Sheets

(56) References Cited

U.S. PATENT DOCUMENTS

| | | |
|---|---|---|
| 6,748,251 B2 | 6/2004 | Tsenkova |
| 9,962,090 B2 | 5/2018 | Dimaio |
| 2003/0166996 A1* | 9/2003 | Kim ................. A61B 5/352 600/300 |
| 2004/0023612 A1* | 2/2004 | Kriesel ................. G06V 20/64 452/157 |
| 2006/0036419 A1 | 2/2006 | Cook |
| 2006/0041408 A1 | 2/2006 | McGoogan |
| 2006/0054092 A1 | 3/2006 | Valencia |
| 2007/0024946 A1 | 2/2007 | Panasyuk |
| 2007/0093965 A1* | 4/2007 | Harrison ............... A01K 29/005 703/11 |
| 2007/0224694 A1* | 9/2007 | Puchalski ............. G01J 3/2823 436/171 |
| 2008/0257830 A1* | 10/2008 | Wu ................. A01K 61/13 210/748.03 |
| 2011/0093232 A1 | 4/2011 | Alber |
| 2011/0093249 A1 | 4/2011 | Holmes |
| 2011/0279650 A1* | 11/2011 | Liao ................. G06V 20/64 348/46 |
| 2016/0018325 A1 | 1/2016 | Elsoee |
| 2016/0069743 A1* | 3/2016 | McQuilkin ............ A22B 5/007 356/416 |
| 2017/0150903 A1* | 6/2017 | Barnes ................. A61B 5/0079 |
| 2017/0303846 A1 | 10/2017 | O'Brien |
| 2018/0047553 A1* | 2/2018 | Richardson ............ A61B 1/041 |
| 2018/0064069 A1 | 3/2018 | Meissner |
| 2018/0085003 A1 | 3/2018 | Goldring |
| 2021/0319460 A1 | 10/2021 | Eden |

FOREIGN PATENT DOCUMENTS

| | | |
|---|---|---|
| EP | 3847436 A1 | 7/2021 |
| JP | 4216077 B2 | 1/2009 |
| JP | 2013508859 A | 3/2013 |
| WO | 2008021103 A2 | 2/2008 |
| WO | 2020051176 A1 | 3/2020 |

* cited by examiner

OPTIMIZING ORGANIC GROWTH USING SPECTRAL MEASUREMENT

This application is a national phase application of PCT/US2019/049438, filed Sep. 4, 2019, and entitled OPTIMIZING ORGANIC GROWTH USING SPECTRIAL MEASUREMENT, which claims the benefit of U.S. Provisional Patent Application No. 62/728,332, filed Sep. 7, 2018 and entitled OPTIMIZING ORGANIC GROWTH USING SPECTRIAL MEASUREMENT, each of which is hereby incorporated by reference in its entirety.

TECHNICAL FIELD

This document pertains generally, but not by way of limitation, to optimizing growth of livestock using non-invasive measuring means to compare a current set of scanned biological parameters to preset chemometric data that is predictive of that livestock's present or future state productive performance conditions.

BACKGROUND

Management of livestock typically endeavors to optimize the yield of each individual livestock when it comes to market via on feed, medical or pharmaceutical care processes to keep each animal growing and healthy. There is a problem however, that each livestock is subjected to a significant number of other growth or yield inputs during its premarket lifespan and that those various combinations of inputs result in a wide variance of market yields of similar livestock despite having similar feed, medical treatment and preventive care.

SUMMARY

The present inventors have recognized, among other things that a solution of this problem include ongoing measurement of the livestock with non-invasive means using spectral scanning of livestock and/or their excreta (individually or collectively). Also, the present inventors recognize that the correlation of these scanning measurements with a data set of previously measured livestock scans allows the consistent compilation of various growth factors that also result in a measure of the potential yield of an individual livestock. These ongoing spectra measurements can also be correlated with any other ongoing monitoring solutions of each/aggregated livestock to provide feedback or metrics on feed, water, health, environmental conditions or pharmaceutical efficacy. By example, scanning feeder pigs with a portable spectrometer through a portion of their premarket lifespan to estimate or diagnose several aspects characterizing their growth is a concrete expression of this solution. The present subject matter can help provide an additional solution to this problem, such as by use of ongoing spectra scanning of livestock and correlation to a detectable health condition or potential associated comorbidity condition. Another manner of describing this solution would be to describe at an early stage a "good" animal to continue its current course of feed, water, supplementation, or a "bad" animal that would be flagged for remedial treatment, additional feed, water, supplementation or diversion to another processing stream.

There are several aspects to this solution that the inventors have established. The first aspect of this solution is that using livestock spectral emissions at various stages of growth to classify individual animals against an established set of premeasured normative metrics. (i.e. a "good" animal for the use intended (good animal) vs. an "bad" animal that will result in a poor yield for the use intended (bad animal.) This first aspect allows the animal owner to selectively change feed, water, or supplementation, or divert the bad animal portions of the group of animals to optimize the market potential of the group, saving feed, energy and other resources that would otherwise be used to raise a "bad animal." Another second aspect is the case where a "bad" animal is identified, a feed differential may be measured between a "good" animal where the goal is to raise both "good and "bad" animals to a general media value rather than to maximize each animal. The second aspect in this case would be to drive each animal to that median value by decreasing/increasing various feed/water/supplementation. A third aspect is that this scanned information would also inform a secondary decision by a lower skilled worker that that normally would be reserved for a veterinary analysis. It is easy to appreciate the benefit of removing the need/cost for a veterinarian analysis for each animal/herd. This third aspect of the solution would allow an untrained animal handler to make informed choices and change feed, water, supplementation, without incurring an additional cost or time required for a highly skilled veterinarian technician. A fourth aspect of the solution is that using a portable spectrometer that allows many variants of spectral measurements to be made on the animal in its normal habitat. The immediate benefit of this fourth aspect in field measurement allows an unstressed animal measurement to occur in the natural surroundings of the animal. This fourth aspect further includes the aspect of using the portable spectrometer to be utilized on the measured animal's dermis, skin or fur as well as being used on a specific type of excreta of that measured animal. A fifth aspect of this solution is that the spectral measurements may be combined with other standard metrics, weight, feed consumed, body temperature, environmental metrics and other measure conditions to enhance the value of those standard metrics. The sixth aspect of the solution could represent any combination of the first five aspects that would also identify a health metric in addition to or in lieu of a "good animal" or "bad animal" metric that would help move a "bad" animal parameter trending to a "good animal" threshold or move a "good" animal parameter to a median animal parameter. More specifically each of these aspects can used in the following manner: The first aspect can include or use subject matter (such as an apparatus, a system, a device, a method, a means for performing acts, or a device readable medium including instructions that, when performed by the device, can cause the device to perform acts, or an article of manufacture), such as can include or use the first and the second aspect of the solution.

The second aspect can include or use or can optionally be combined with the subject matter of the first aspect, to optionally include or use the third aspect.

The third aspect can include or use, or can optionally be combined with the subject matter of one or any combination of aspects 1 or 2 to optionally include or use a spectral reading to determine a health metric for a veterinary purpose, moisture or feed deficiency.

The fourth aspect can include, or can optionally be combined with the subject matter of one or any combination of Aspects 1 through 3 to include or use, subject matter (such as an apparatus, a method, a means for performing acts, or a machine readable medium including instructions that, when performed by the machine, that can cause the machine to perform acts), such as can be correlated to provide an ongoing market and health performance review of the animal.

The fifth aspect can include, or can optionally be combined with the subject matter of one or any combination of Aspects 1 through 4 to include or use, subject matter (such as an apparatus, a method, a means for performing acts, or a machine readable medium including instructions that, when performed by the machine, that can cause the machine to perform acts), such as can be correlated to provide an ongoing market and health performance review of the animal.

The sixth aspect can include, or can optionally be combined with the subject matter of one or any combination of Aspects 1 through 5 to include or use, subject matter (such as an apparatus, a method, a means for performing acts, or a machine readable medium including instructions that, when performed by the machine, that can cause the machine to perform acts), such as can be correlated to provide an ongoing market and health performance review of the animal. This presents a system for measuring a market performance metric of an animal comprising a sensor unit that detects an emitted spectrum from the animal wherein the sensor unit filters the received emitted spectra to a set of spectral values; and a memory unit that comprises a set of predetermined chemometric data correlated to at least a market performance metric, wherein the memory unit is correlated to the set of spectral values.

Such subject matter can include or use a means for a portable spectral measurement, illustrative examples of which can include 1) a portable device comprising at least a sensing element that illuminates and records emitted spectra of a target animal and writes it to a local memory on the device, the device including a mobile phone with spectral sensor or the camera element of that mobile phone optimized to sense a useful set of spectra for this solution; 2) a portable device as described in 1) that also transmits in real time, or in batch, recorded spectra via wireless, wired or cellular means, the measurements associated with a particular animal to a remote server that contains a corpus of market descriptors pertaining to that particular animal as well as a reference set of norms for that class; and/or 3) a remote server as described in 2) that transmits back to the portable device or another display on another user device, a set of values corresponding to a health metric, a market metric, environmental metric or an advisory metric for the particular animal.

Each of these non-limiting examples can stand on its own or can be combined in various permutations or combinations with one or more of the other examples.

This overview is intended to provide an overview of subject matter of the present patent application. It is not intended to provide an exclusive or exhaustive explanation of the invention. The detailed description is included to provide further information about the present patent application.

Figure 1:
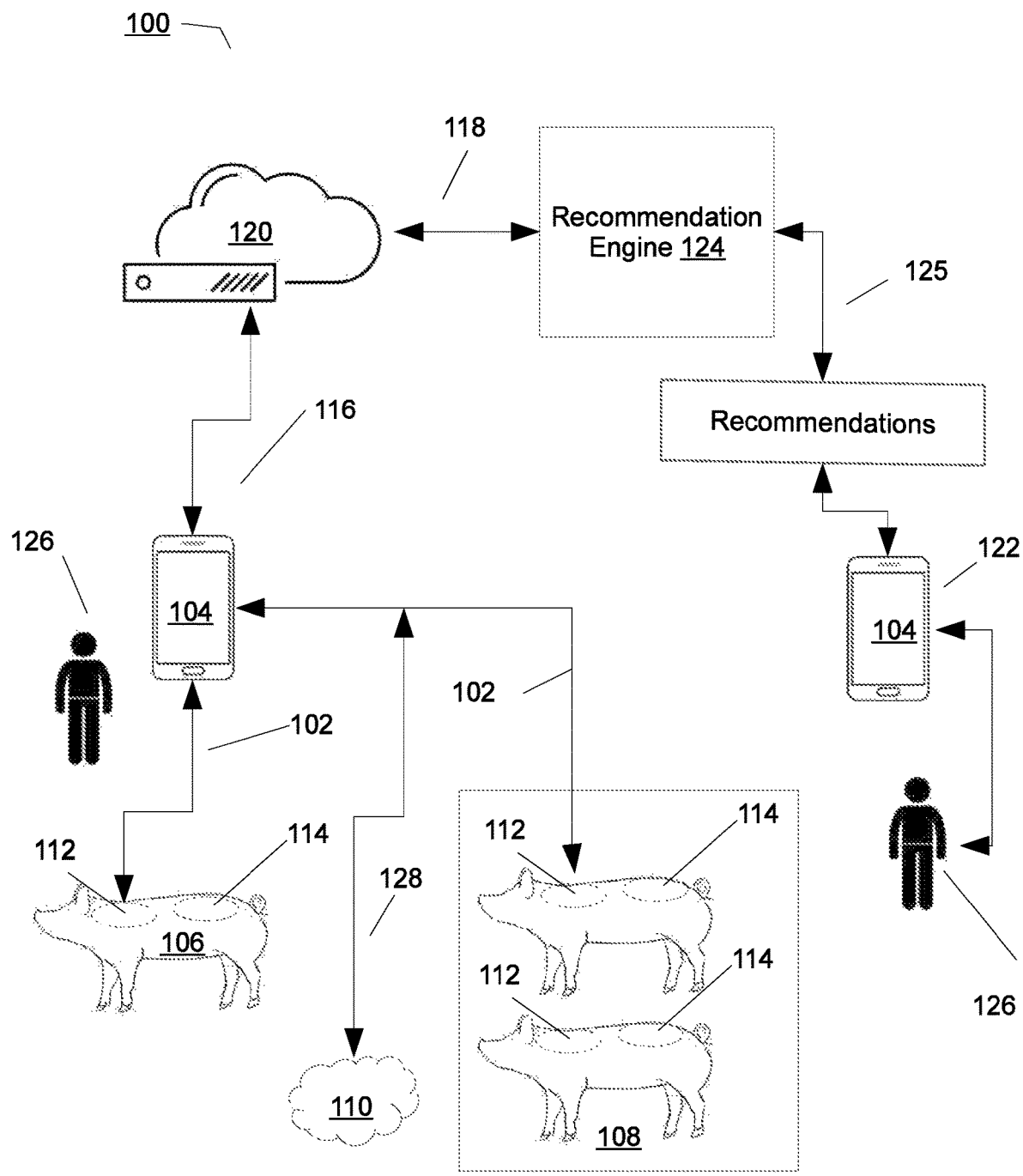
FIG. 1 illustrates a functional diagram of a scan in accordance with some embodiments.

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

Embodiments of this solution may be implemented in one or a combination of hardware, firmware and software. Embodiments may also be implemented as instructions stored on a computer-readable storage device, which may be read and executed by at least one processor to perform the operations described herein. A computer-readable storage device may include any non-transitory mechanism for storing information in a form readable by a machine (e.g., a computer). For example, a computer-readable storage device may include read-only memory (ROM), random-access memory (RAM), magnetic disk storage media, optical storage media, flash-memory devices, cloud servers or other storage devices and media. Some embodiments may include one or more processors and may be configured with instructions stored on a computer-readable storage device. The following description and the referenced drawings sufficiently illustrate specific embodiments to enable those skilled in the art to practice them. Other embodiments may incorporate structural, logical, electrical, process, and other changes. Portions and features of some embodiments may be included in, or substituted for, those of other embodiments. Embodiments set forth in the claims encompass all available equivalents of those claims.

Definitions of Terms Used in this Description

Market performance metric: a value that indicates a correlated value between a measured value on an animal or its excreta that suggests an outcome for the animal when it is harvested. This includes weight, chemical composition, and any other useful measurement that derives an estimated final market state of a measured animal.

Health metric: a value that indicates a correlated value between a measured value on an animal or its excreta that suggests a health condition of the animal. This health metric includes weight, chemical composition, and any other useful measurement that derives an estimated health state of a measured animal.

Environmental metric: a value that indicates a correlated value between a measured value on an animal or its excreta that suggests an environmentally affected condition of the animal. This environmental metric includes lighting level, airflow, oxygen levels, and any other useful measurement that impacts an estimated health state of a measured animal.

Emitted spectra: Any detectable optical emission from the animal.

Set of spectral values: a filtered set of spectra that allows correlation with chemometric data.

Chemometric data: Chemometrics is the science of extracting information from chemical systems by data-driven means. Chemometrics is inherently interdisciplinary, using methods frequently employed in core data-analytic disciplines such as multivariate statistics, applied mathematics, and computer science, to address problems in chemistry, biochemistry, medicine, biology and chemical engineering. In this solution, the chemometric data is predetermined by experiment or observation and each chemometric model customized to the animal using body weight, body composition, fat depth, loin depth, and other carcass measurements in the case of animals. In the case of this solutions scanning of excreta, the chemometric data is similarly predetermined either at an individual livestock level in experimentation or modeling a group of animals and establish threshold values for acceptable ranges.

Near infrared reflectance spectroscopy (NIRS): Near-infrared spectroscopy (NIRS) is a spectroscopic method that uses the near-infrared region of the electromagnetic spectrum (from '780 nm to 2500 nm). Accurate NIRS calibrations for this solution are based on curated scanned samples representative of the desired outcome.

Excreta: In this solution, the excreta are defined as any waste matter discharged from the body comprising feces, expectorate, sweat, urine or any industry specific term for these waste components.

General Scanning and Classification Process

In FIG. 1, a process for spectra classifying livestock is shown generally 100. This would also be analogous for spectra classifying other types of animals. In the first step 102, the scanning step, sample scans are taken with a spectrometer 104, comparing the most recent scans of an animal 106 to data from known "good animals and known bad animals." If no such known animals are available, a general set of scans of the target population is taken and the results will be evaluated at slaughter to reveal correlations to a scan hypothesis that estimates parameters of the animal 106 and offers comparative values to other group animals 108 in the measured group. Also, the excreta 110 may be scanned with the spectrometer 104. These scan samples preferably include scans, primary scan area (PSA) 112 or secondary scan area (SSA) 114 of the same areas on each animal to establish a baseline, as well as taking scan samples in conditions approximating similar field conditions including scanning method, and timing of the scan in the day. While carefully tracking the known conditions relating to each sample, one or more scans may be taken of each scan area (112 or 114). When taking multiple scans of the same sample animal, one preferably captures a variety of information, on the animal such as estimated weight, fat depth, loin depth, fat content, chemical pigment, nutritional content or coloration)

As scans are taken and associated with the pertinent sample data, in the next step 116, the scans are passed to the analytics server 120 via a communication connection 118 The communication connection 118 may be wired, wireless, or cellular to pass the scans to the analytics server 120 For the sake of clarity, the scan data can be passed in real time, sequentially or in batch format to the analytics server 120. The spectral scans are then reviewed by the analytics server 120 for unique spectral signatures associated with the various animals in the group and potentially other animal groups. The analytics server 120 associates those unique spectral signatures with health metrics or market yield metrics related to the target animal 106. Based on these unique signatures and their associated metrics (e.g., health or market yield) these results are sent via the next step 118 to a recommendation engine 124. The recommendation engine 124 uses the unique spectral signatures associated with health metrics or market yield metrics related to the target animal 106 to make a recommendation for each animal 106 or in the alternative, gives a comparative recommendation relative between various animals in the group (animal 106 vs group animals 108). These recommendations include feed, supplementation, medical treatment, water, environmental conditions, exclusion/cull recommendations. For example, a farrow sow that has diminished back fat when scan would receive a recommendation from the recommendation engine 124 suggesting that the sow should receive a different formulation or amount of various feeds to correct that diminished back fat condition. This change in back fat would then bring the farrow sow back to an optimal farrowing profile for that animal. In another example, a market pig whose scan indicates a deficient back fat profile would also receive a change in feed programming. The recommendation engine 124 would convert a back-fat measurement to a recommendation of a feed, water or environmental change which would assist the market pig in keeping higher energy or lysine content into the market pig to keep its growth performance on track to an optimal market delivery time. In a third example, a piglet scanned at weaning would receive a recommendation from the recommender engine 124 identify and sequester an at-risk piglet into a specialized care diet and supplemental environmental factors to bring that piglet back into a safe growth profile. During the next step 125, the recommendation is passed back to a device (either a spectrometer 104 or another mobile communication device such as a mobile phone) for a recommendation to a care attendant 126 for continued treatment of the animal 106. If the additional step of excreta scanning 128 is performed, the data from follows a similar path as the PSA 112 scan sending data via spectrometer 104 to the communication connection 118 adding the data to the analytics server 120. The excreta scan 128 can also generate independent recommendations for feed, water, environmental, supplementation and health treatments from the recommendation engine 124. The recommendation engine 124 also be queried by a care attendant, 126 to understand previous conditions/recommendations of the scanned animal 106, query a current observed condition 122, or to log actions taken in line with the recommendations. Generally, animal scanning processes are repeated at regular intervals under similar conditions.

Figure 2:
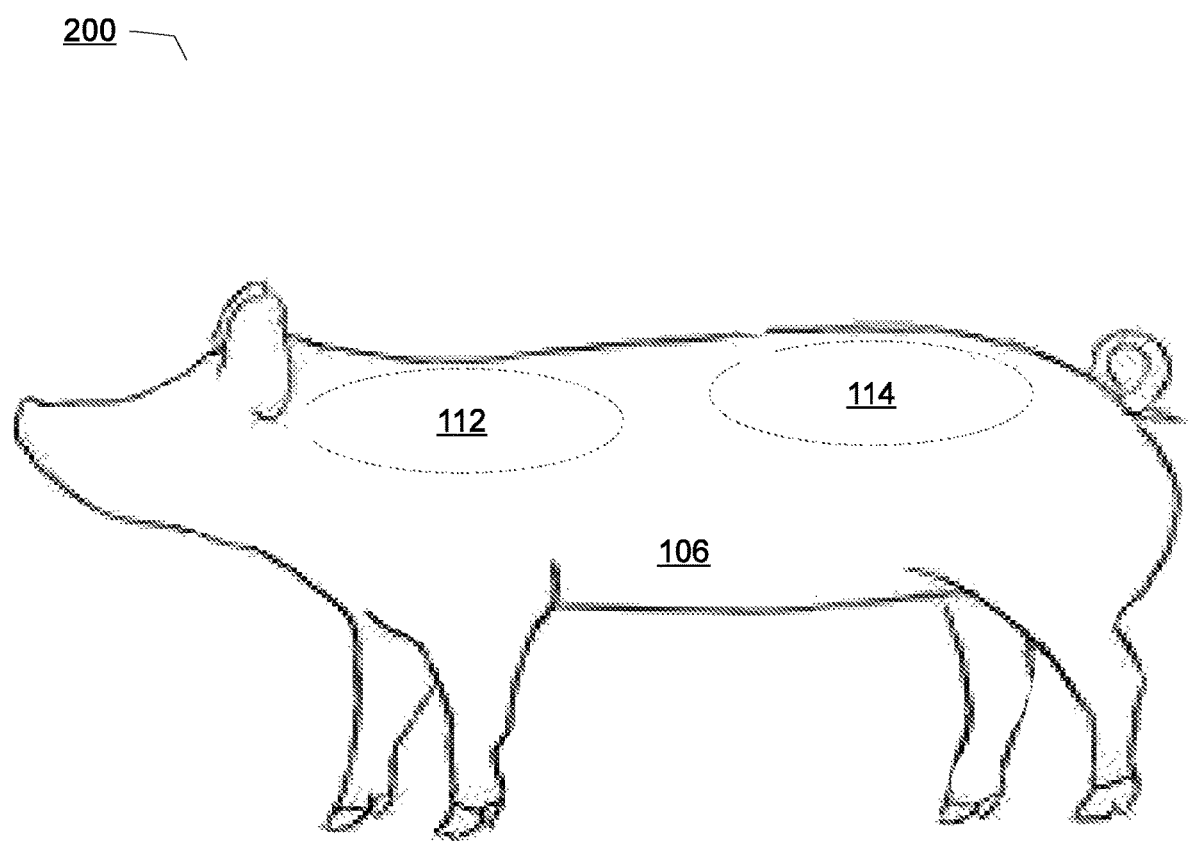
FIG. 2 illustrates beneficial scanning areas on swine and its excreta in accordance with some embodiments.

Scanning Protocols for Swine or Pigs:

Useful scanning areas on a Pig 200 are noted in FIG. 2 defined by PSA 112 and SSA 114 for the scanning step 102. These areas are beneficial as they provide regions of thinner hair for more accurate readings and they correspond to various market correlations for meat production. They also have good correlation to deliver health assessment results. The primary assessment location PSA 112 is in the shoulder area as noted. The PSA 112 location allows measurement of the loin depth and back fat. The SSA 114 near or around the $10^{th}$ or last rib on the animal also can be used to estimate body weight when combining with the animal age and gender. Scans take between 5-15 seconds per scan to complete. The excreta scan 128 can be correlated to average feed intake, nutrient concentration (e.g. protein moisture), indicators of digestive health (pH, osmolality, ammonia, certain metabolites (e.g. butyrate)), fecal matrix that increases probability of certain microflora (e.g. *E coli, E coli/lactobacillus* ratio).

Overall scan frequency can be performed in an ad hoc manner or any periodic cycle that helps to adjust feed or estimate weight. Scan initiation and repeat frequency would vary depending on what market parameter or health parameter is being checked. For example, "Good"/"Bad" scans 102 would initiate from the peri-weaning time which allows useful changes and the time to fix the standard problems. Excreta scanning 128 would also initiate peri-weaning to allow time and process to have an effect on the production cycle. Body composition scanning would likely happen later in the production cycle.

Excreta Scanning Process and Benefits

This is a powerful feedback aspect of the solution. The excreta scan comprises a scan of the feed, the animal ingesting the feed, as a scan on nutritional remainder in the excreta. In general, the spectral scanning of animal excreta to determine dietary health of the livestock will generally be made in an aggregate format (collected excreta from a defined group of livestock) but could be aligned to specific livestock if the value of the data acquisition is justified by the value of the individual livestock. The spectral information will be compared with the chemometric data gathered to represent the prescribed feed type and a predicted composition. Any scan result outside the defined margin of error is would be resolved into a feed, water, environmental, or supplementation recommendation or a request to review whether the animal is receiving the correct feed type or supplementation. This recommendation benefits the producer of this livestock as a traditional chemical analysis would not be real-time, require a lab analysis and the interpretation of this information requires some nutritional expertise, especially when feeds are to be mixed or supplemented, to meet production requirements. Minimizing the cost of professional nutrition analysis which is an important component of any feed analysis system, especially when excreta yield unexpected analytical results is of a benefit of this solution. This feedback from the excreta is particularly useful when most livestock scans fall within acceptable values but begin trending toward bad values. This solution can offer real-time suggestions for changes before the group of livestock transitions to an unacceptable range. This solution allows the feed and supplementation process to make small changes to optimally control the livestock growth envelope more completely using NIRS Chemometric data of both the composition of the feed prior to ingestion by the livestock and subsequent evaluation of the livestock excreta to optimize the feeding and supplementation strategy as well as cost benefit calculations of when supplements aren't necessary.

Figure 3:
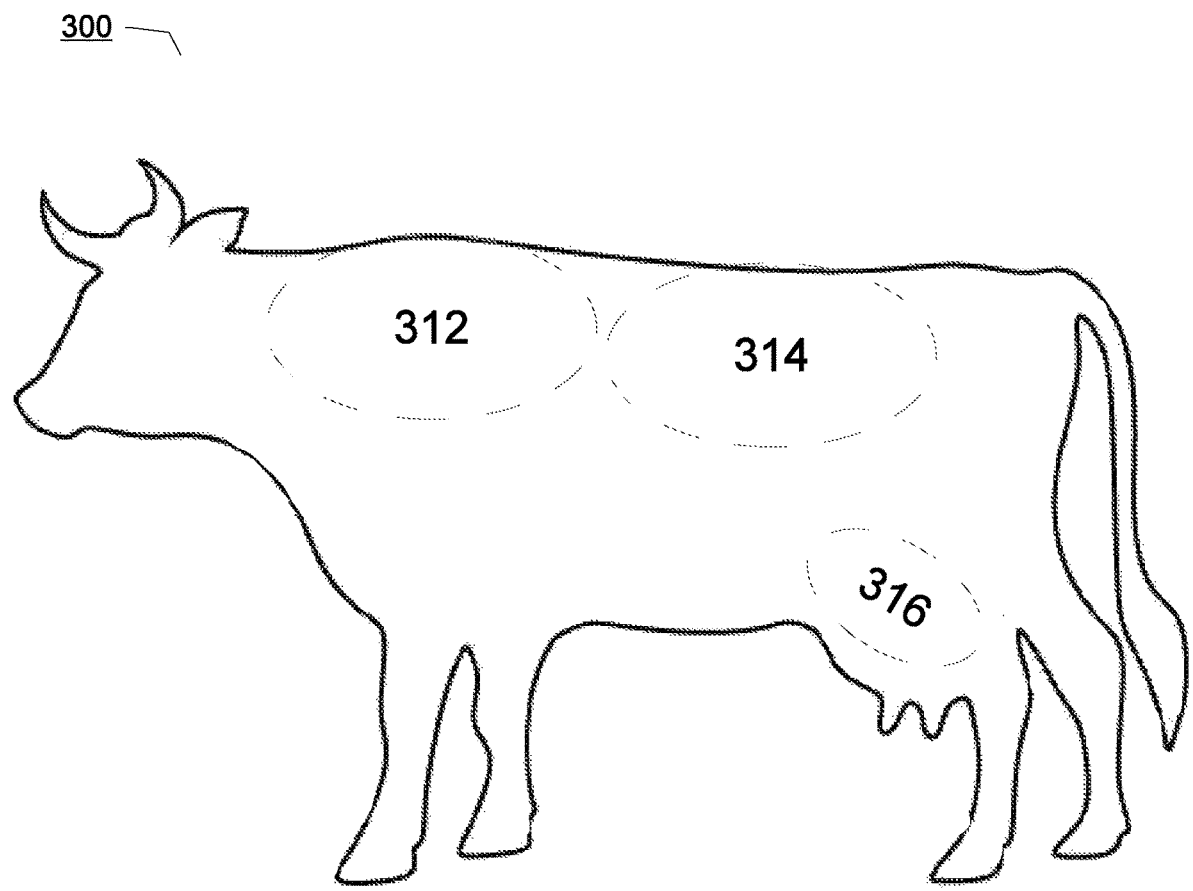
FIG. 3 illustrates beneficial scanning areas on bovines and its excreta in accordance with some embodiments.

Scanning Protocols for Bovines or Cattle:

As mentioned earlier, scanning process is analogous to many animal types. Useful scanning areas on a bovine or cow 300 are noted in FIG. 3. As defined by cow primary scanning area (CPSA) 312 and cow secondary scanning area (CSSA) 314 for the analogous scanning step 102 as referenced in FIG. 1. These areas are beneficial as they provide areas of thinner hair for more accurate scan readings and they correspond to various market correlations for beef cattle production. In the case of dairy cattle production an additional dairy scanning area 316 near or on the udder is defined. To the degree required by the type of cow, hair may need to be removed to provide useful scans. These referenced scan areas (312,314,316) also provide good correlation to deliver health assessment results. The primary assessment location 312 is in the shoulder area as noted. The secondary assessment location allows measurement of the loin depth and back fat. The secondary assessment location 314 near the 10th or last rib on the animal also can be used to estimate body weight when combining with the animal age and gender. Scans take between 5-15 seconds per scan to complete. The excreta scans can be correlated to average feed intake, nutrient concentration (e.g. protein moisture), indicators of digestive health (pH, osmolality, ammonia, certain metabolites (e.g. butyrate)), fecal matrix that increases probability of certain microflora (e.g. *E coli, E coli/lactobacillus* ratio)

Overall scan frequency can be performed in an ad hoc manner or any periodic cycle that helps to adjust feed or estimate weight Scan initiation and repeat frequency would vary depending on what market parameter or health parameter is being checked. For example, "Good"/"Bad" scans would initiate from the peri-weaning time which allows useful changes and the time to fix the standard problems. In the case of dairy cattle, scanning would begin post freshening. Excreta scanning 128 would also initiate peri-weaning to allow time and process to have an effect on the production cycle Body composition scanning would likely happen later in the production cycle.

Scanning Protocols for Poultry

Figure 4:
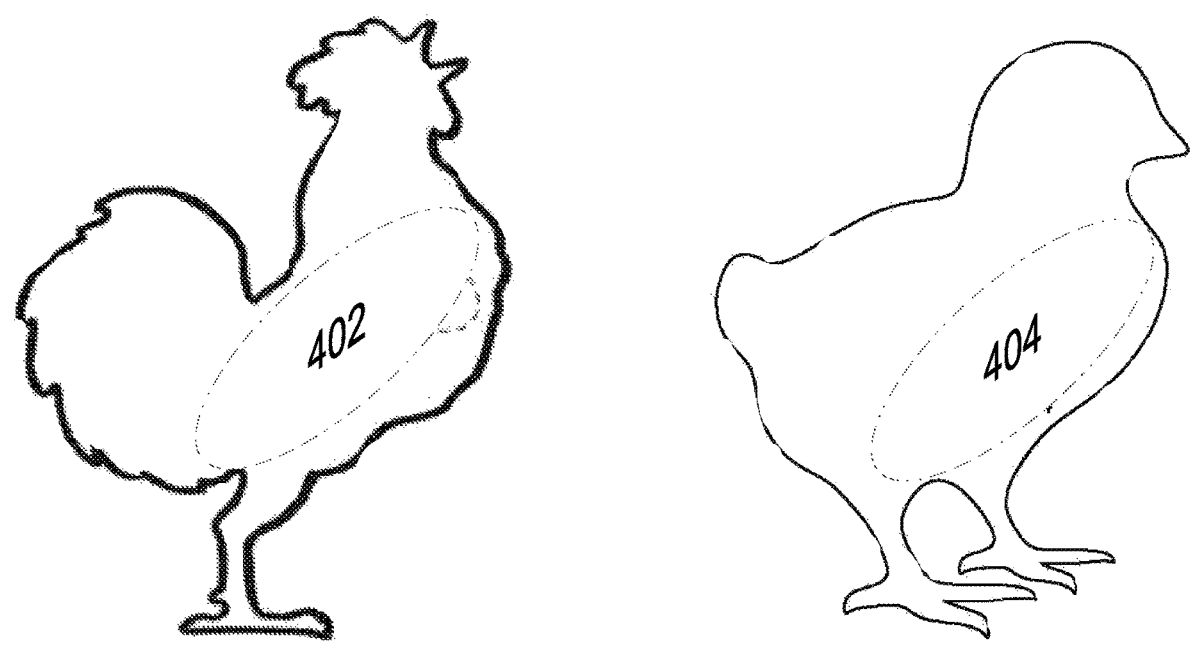
FIG. 4 illustrates beneficial scanning areas on poultry and its excreta in accordance with some embodiments.

Useful scanning areas on an adult chicken 402 or pullet 404 is noted in FIG. 4, in the abdomen/groin area and would require feather free areas for scanning. These areas are beneficial as they provide measurements of fat pad weight, body weight, or body composition. The scan areas also provide good correlation to deliver health assessment results. Scans take between 5-15 seconds per scan to complete. Additional uses would provide enhanced management decisions (e.g. lighting interval), optimize onset of laying, prediction of slaughter measures in broilers.

The excreta scans can be correlated to average feed intake, nutrient digestibility, nutrient concentration (e.g. protein moisture), indicators of digestive health (pH, osmolality, ammonia, certain metabolites (e.g. butyrate)), fecal matrix that increases probability of certain microflora (e.g. *E coli, E coli/lactobacillus* ratio).

Overall scan frequency can be performed in an ad hoc manner or any periodic cycle that helps to adjust feed or estimate weight. Generally, these scans can be performed at any time given but predominantly when rearing issue would most likely initiate, both from a production and physiological perspective.

Aquaculture Scanning of Aquatic Livestock

Figure 5A:
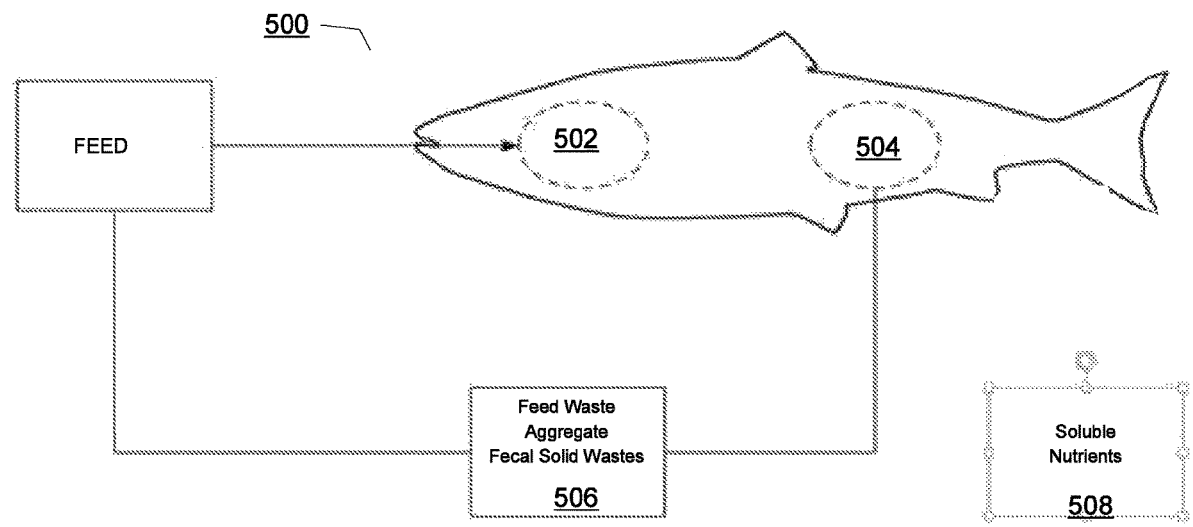
FIG. 5a illustrates beneficial scanning areas on finned species and its excreta in accordance with some embodiments.
Figure 5B:
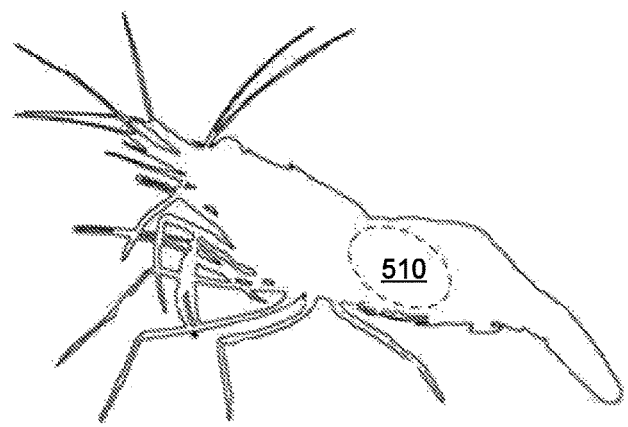
FIG. 5b illustrates beneficial scanning areas on crustacea in accordance with some embodiments.

As shown in FIGS. 5a and 5b, this solution also is useful for aquaculture species comprising Salmonid 500, Crustacea 501 and related commercially useful amphibious, reptilian or finfish farming species Due to the size of most aquaculture species, this solution technique is adapted to sample a number of livestock from the group and using that sample to create inferences about the full group rather than testing each animal. The benefits of using NIRS scans are revealed by extracting additional information about the group of fish that aren't generally measured while live, comprising determining proximates content, lipid content, vitamin ratios, mineral ratios, flesh color, and amino mix and amino concentrations in the living animal. Measuring these variables allows this solution to be used for optimizing aquaculture species for specific consumer preferences of color, creating wild species nutritional equivalents in farmed species. (See; United States Department of Agriculture's National Nutrient Database for Standard Reference Legacy Release) as well as minimizing post-harvest chemical/nutritional testing costs. Another benefit of this NIRS solution would allow detection of undesired minerals that might indicate the existence of contaminants or other organisms. This solution would comprise correlations based on nutrients or parameters like pH, alkalinity, ammonia, nitrite, or other chemical concentrations that would indicate the potential for a specific bacteria or organism as well as water quality for that is optimized for the particular species.

Scanning Protocols for Aqua Culture Species

Useful scanning areas on a finned species or a Crustacea species are noted in FIGS. 5a and 5b near the gill area 502 or abdomen area 504, 510 for scanning. These areas are beneficial as they provide measurements of body weight, or body composition that would result in a number of market estimates such as growth rate, flesh color, bio-mineralization level of shell or scale. The scan areas also provide good correlation to deliver health assessment results. Scans take between 5-15 seconds per scan to complete.

The excreta scan 506 as described in the solid excreta can be correlated to average feed intake, nutrient digestibility, and nutrient concentration. Soluble Nutrients 508 may be inferred by measuring particle size or water turbidity with the Spectrograph 600.

Overall scan frequency can be performed in an ad hoc manner or any periodic cycle that helps to adjust feed or estimate weight. Generally, these scans can be performed at any time; however, meat or protein content would be done later in the production cycle nearing the market readiness of the aquatic animal.

Device Apparatus and Configurations

Figure 6:
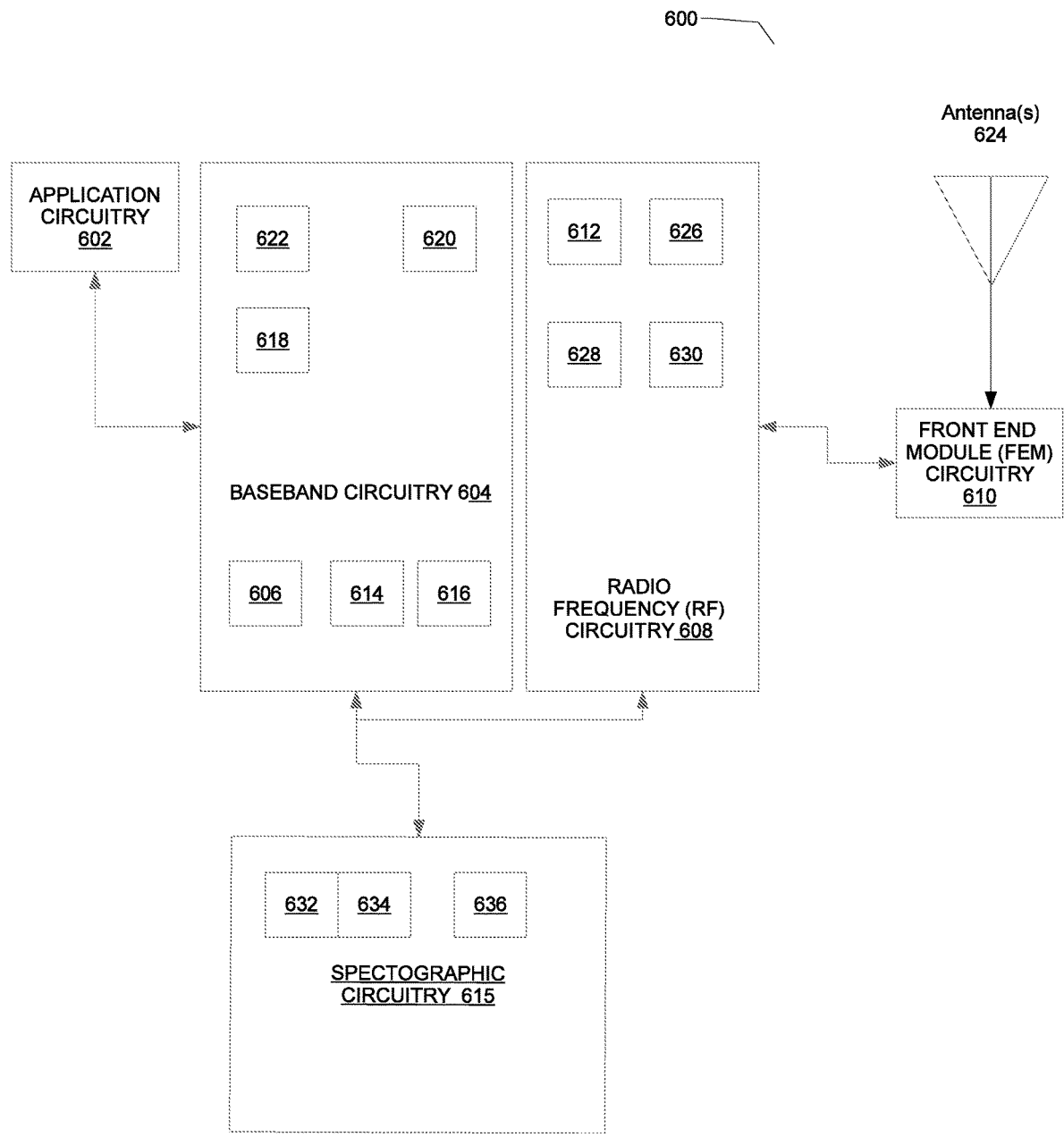
FIG. 6 illustrates an aspect of the hardware of a spectrometer in accordance with some embodiments.

Turning to the Drawings, FIG. 6 illustrates example components of the spectrometer 600 in accordance with some embodiments. In some embodiments, the spectrometer 600 may include Application circuitry 602, Baseband Circuitry 604, Radio Frequency (RF) circuitry 608, front-end Front-End Module (FEM) circuitry 608, Spectrographic circuitry 615 and one or more antennas 624, coupled together at least as shown.

The Application circuitry 602 may include one or more application processors. For example, the Application circuitry 602 may include circuitry such as, but not limited to, one or more single-core or multi-core processors. The processor(s) may include any combination of general-purpose processors and dedicated processors (e.g., graphics processors, application processors, etc.). The processors may be coupled with and/or may include memory/storage and may be configured to execute instructions stored in the memory/storage to enable various applications and/or operating systems to run on the system.

The Spectrographic circuitry 615 may include one or more application processors. For example, the Spectrographic circuitry 615 may include circuitry such as, but not limited to, one or more single-core or multi-core processors. The processor(s) may include any combination of general-purpose processors and dedicated processors (e.g., graphics processors, application processors, etc.). The processors may be coupled with and/or may include memory/storage and may be configured to execute instructions stored in the memory/storage to enable various applications and/or operating systems to run on the system and utilize hardware related to creating and processing a spectrographic reading. In some embodiments, the spectrographic circuitry 615 is attachable to a device such as a mobile device rather than integrated into a single unit spectrograph 600.

The Baseband Circuitry 604 may include circuitry such as, but not limited to, one or more single-core or multi-core processors. The Baseband Circuitry 604 may include one or more baseband processors and/or control logic to process baseband signals received from a receive signal path of the Radio Frequency (RF) circuitry 608 and to generate baseband signals for a transmit signal path of the Radio Frequency (RF) circuitry 608. Baseband Circuitry 604 may interface with the Application circuitry 602 for generation and processing of the baseband signals and for controlling operations of the Radio Frequency (RF) circuitry 608. For example, in some embodiments, the Baseband Circuitry 604 may include a second generation (2G) baseband processor 606, third generation (3G) baseband processor 614, fourth generation (4G) baseband processor 616, and/or other baseband processor(s) 618 for other existing generations, generations in development or to be developed in the future (e.g., fifth generation (5G), 6G, etc.). The Baseband Circuitry 604 (e.g., one or more of baseband processors 606, 614,616,618) may handle various radio control functions that enable communication with one or more radio networks via the Radio Frequency (RF) circuitry 608. The radio control functions may include, but are not limited to, signal modulation/demodulation, encoding/decoding, radio frequency shifting, etc. In some embodiments, modulation/demodulation circuitry of the Baseband Circuitry 604 may include Fast-Fourier Transform (FFT), precoding, and/or constellation mapping/demapping functionality. In some embodiments, encoding/decoding circuitry of the Baseband Circuitry 604 may include convolution, tail-biting convolution, turbo, Viterbi, and/or Low-Density Parity Check (LDPC) encoder/decoder functionality. Embodiments of modulation/demodulation and encoder/decoder functionality are not limited to these examples and may include other suitable functionality in other embodiments.

In some embodiments, the Baseband Circuitry 604 may include elements of a protocol stack such as, for example, elements of an evolved universal terrestrial radio access network (EUTRAN) protocol including, for example, physical (PHY), media access control (MAC), radio link control (RLC), packet data convergence protocol (PDCP), and/or radio resource control (RRC) elements. A central processing unit (CPU) 620 of the Baseband Circuitry 604 may be configured to run elements of the protocol stack for signaling of the PHY, MAC, RLC, PDCP and/or RRC layers. In some embodiments, the baseband circuitry may include one or more audio digital signal processor(s) (DSP) 622. The audio DSP(s) 622 may include elements for compression/decompression and echo cancellation and may include other suitable processing elements in other embodiments. Components of the baseband circuitry may be suitably combined in a single chip, a single chipset, or disposed on a same circuit board in some embodiments. In some embodiments, some or all of the constituent components of the Baseband Circuitry 604 and the Application circuitry 602 may be implemented together such as, for example, on a system on a chip (SOC).

In some embodiments, the Baseband Circuitry 604 may provide for communication compatible with one or more radio technologies. For example, in some embodiments, the Baseband Circuitry 604 may support communication with an evolved universal terrestrial radio access network (EUTRAN) and/or other wireless metropolitan area networks (WMAN), a wireless local area network (WLAN), a wireless personal area network (WPAN). Embodiments in which the Baseband Circuitry 604 is configured to support radio communications of more than one wireless protocol may be referred to as multi-mode baseband circuitry.

Radio Frequency (RF) circuitry 608 may enable communication with wireless networks using modulated electromagnetic radiation through a non-solid medium. In various embodiments, the Radio Frequency (RF) circuitry 608 may include switches, filters, amplifiers, etc. to facilitate the communication with the wireless network. Radio Frequency (RF) circuitry 608 may include a receive signal path which may include circuitry to down-convert RF signals received from the FEM circuitry 610 and provide baseband signals to the Baseband Circuitry 604. Radio Frequency (RF) circuitry 608 may also include a transmit signal path which may include circuitry to up-convert baseband signals provided by the Baseband Circuitry 604 and provide RF output signals to the Front-End Module (FEM) circuitry 610 for transmission.

In some embodiments, the Radio Frequency (RF) circuitry 608 may include a receive signal path and a transmit signal path. The receive signal path of the Radio Frequency (RF) circuitry 608 may include mixer circuitry 612, amplifier circuitry 626 and filter circuitry 628. The transmit signal path of the Radio Frequency (RF) circuitry 608 may include filter circuitry 628 and mixer circuitry 612. Radio Frequency (RF) circuitry 608 may also include synthesizer circuitry 630 for synthesizing a frequency for use by the mixer circuitry 612 of the receive signal path and the transmit signal path. In some embodiments, the mixer circuitry 612 of the receive signal path may be configured to down-convert RF signals received from the Front-End Module (FEM) circuitry 610 based on the synthesized frequency provided by synthesizer circuitry 630.

The amplifier circuitry 626 may be configured to amplify the down-converted signals and the filter circuitry 628 may be a low-pass filter (LPF) or band-pass filter (BPF) configured to remove unwanted signals from the down-converted signals to generate Output baseband signals. Output baseband signals may be provided to the Baseband Circuitry 604 for further processing. In some embodiments, the Output baseband signals may be zero-frequency baseband signals, although this is not a requirement. In some embodiments, mixer circuitry 612 of the receive signal path may comprise passive mixers, although the scope of the embodiments is not limited in this respect.

In some embodiments, the mixer circuitry 612 of the transmit signal path may be configured to up-convert Input baseband signals based on the synthesized frequency provided by the synthesizer circuitry 630 to generate RF Output signals for the Front-End Module (FEM) circuitry 610. The baseband signals may be provided by the Baseband Circuitry 604 and may be filtered by filter circuitry 628. The filter circuitry 628 may include a low-pass filter (LPF), although the scope of the embodiments is not limited in this respect.

In some embodiments, the mixer circuitry 612 of the receive signal path and the mixer circuitry 612 of the transmit signal path may include two or more mixers and may be arranged for quadrature down-conversion and/or up-conversion respectively. In some embodiments, the mixer circuitry 612 of the receive signal path and the mixer circuitry 612 of the transmit signal path may include two or more mixers and may be arranged for image rejection (e.g., Hartley image rejection). In some embodiments, the mixer circuitry 612 of the receive signal path and the mixer circuitry 612 may be arranged for direct down-conversion and/or direct up-conversion, respectively. In some embodiments, the mixer circuitry 612 of the receive signal path and the mixer circuitry 612 of the transmit signal path may be configured for super-heterodyne operation.

In some embodiments, the Output baseband signals and the Input baseband signals may be analog baseband signals, although the scope of the embodiments is not limited in this respect. In some alternate embodiments, the Output baseband signals and the Input baseband signals may be digital baseband signals. In these alternate embodiments, the Radio Frequency (RF) circuitry 608 may include analog-to-digital converter (ADC) and digital-to-analog converter (DAC) circuitry and the Baseband Circuitry 604 may include a digital baseband interface to communicate with the Radio Frequency (RF) circuitry 608.

In some dual-mode embodiments, a separate radio IC circuitry may be provided for processing signals for each spectrum, although the scope of the embodiments is not limited in this respect.

In some embodiments, the synthesizer circuitry 630 may be a fractional-N synthesizer or a fractional N IN+1 synthesizer, although the scope of the embodiments is not limited in this respect as other types of frequency synthesizers may be suitable. For example, synthesizer circuitry 630 may be a delta-sigma synthesizer, a frequency multiplier, or a synthesizer comprising a phase-locked loop with a frequency divider.

The synthesizer circuitry 630 may be configured to synthesize an Output frequency for use by the mixer circuitry 612 of the Radio Frequency (RF) circuitry 608 based on a frequency Input and a divider control Input. In some embodiments, the synthesizer circuitry 630 may be a fractional N IN+1 synthesizer.

In some embodiments, frequency input may be provided by a voltage-controlled oscillator (VCO), although that is not a requirement. Divider control Input may be provided by either the Baseband Circuitry 604 or the applications processor in Application circuitry 602 depending on the desired Output frequency. In some embodiments, a divider control Input (e.g., N) may be determined from a look-up table based on a channel indicated by the applications processor in Application circuitry 602.

Synthesizer circuitry 630 of the Radio Frequency (RF) circuitry 608 may include a divider, a delay-locked loop (DLL), a multiplexer and a phase accumulator. In some embodiments, the divider may be a dual modulus divider (DMD) and the phase accumulator may be a digital phase accumulator (DPA). In some embodiments, the DMD may be configured to divide the Input signal by either N or N+1 (e.g., based on a carry out) to provide a fractional division ratio. In some example embodiments, the DLL may include a set of cascaded, tunable, delay elements, a phase detector, a charge pump and a D-type flip-flop. In these embodiments, the delay elements may be configured to break a VCO period up into Nd equal packets of phase, where Nd is the number of delay elements in the delay line. In this way, the DLL provides negative feedback to help ensure that the total delay through the delay line is one VCO cycle.

In some embodiments, synthesizer circuitry 630 may be configured to generate a carrier frequency as the Output frequency, while in other embodiments, the Output frequency may be a multiple of the carrier frequency (e.g., twice the carrier frequency, four times the carrier frequency) and used in conjunction with quadrature generator and divider circuitry to generate multiple signals at the carrier frequency with multiple different phases with respect to each other.

In some embodiments, the Output frequency may be a LO frequency (fLO). In some embodiments, the Radio Frequency (RF) circuitry 608 may include an IQ/polar converter.

Front End Module (FEM) circuitry 610 may include a receive signal path which may include circuitry configured to operate on RF signals received from one or more antennas 624, amplify the received signals and provide the amplified versions of the received signals to the Radio Frequency (RF) circuitry 608 for further processing. Front End Module (FEM) circuitry 610 may also include a transmit signal path which may include circuitry configured to amplify signals for transmission provided by the Radio Frequency (RF) circuitry 608 for transmission by one or more of the one or more antennas 624.

In some embodiments, the Front-End Module (FEM) circuitry 610 may include a TX/RX switch to switch between transmit mode and receive mode operation. The FEM circuitry may include a receive signal path and a transmit signal path. The receive signal path of the FEM circuitry may include a low-noise amplifier (LNA) to amplify received RF signals and provide the amplified received RF signals as an Output (e.g., to the Radio Frequency (RF) circuitry 608). The transmit signal path of the Front-End Module (FEM) circuitry 610 may include a power amplifier (PA) to amplify Input RF signals (e.g., provided by Radio Frequency (RF) circuitry 608), and one or more filters to generate RF signals for subsequent transmission (e.g., by one or more of the one or more antennas 624.

In some embodiments, the Spectrographic circuitry 615, includes a surface scanning biometric sensor 632 which includes: a light source unit 634 configured to project an excitation illumination to a target animal; a spectrometer configured to measure a spectrum distribution of a reflected light generated from the object by the excitation illumination; and a spectrographic controller 636 configured to control operations of the spectrometer and record spectral properties of the target animal by using signals provided by the spectrometer, the spectrometer including: a light absorbing structure including a plurality of absorbing layers, the layers having different absorption wavelength bands, and a plurality of tunnel junction layers respectively interposed between the plurality of absorbing layers to electrically connect the plurality of absorbing layers; and an illuminating unit configured to select an absorbing layer from among the plurality of absorbing layers and provide the light absorbing structure with an illumination light including the absorption wavelength bands of the other absorbing layers, other than the absorption wavelength band of the selected absorbing layer.

In some embodiments, the spectrometer 600 may include additional elements such as, for example, memory/storage, display, GPS camera, sensor, and/or Input/Output (I/O) interface.

Data Transmission Apparatus

Figure 7:
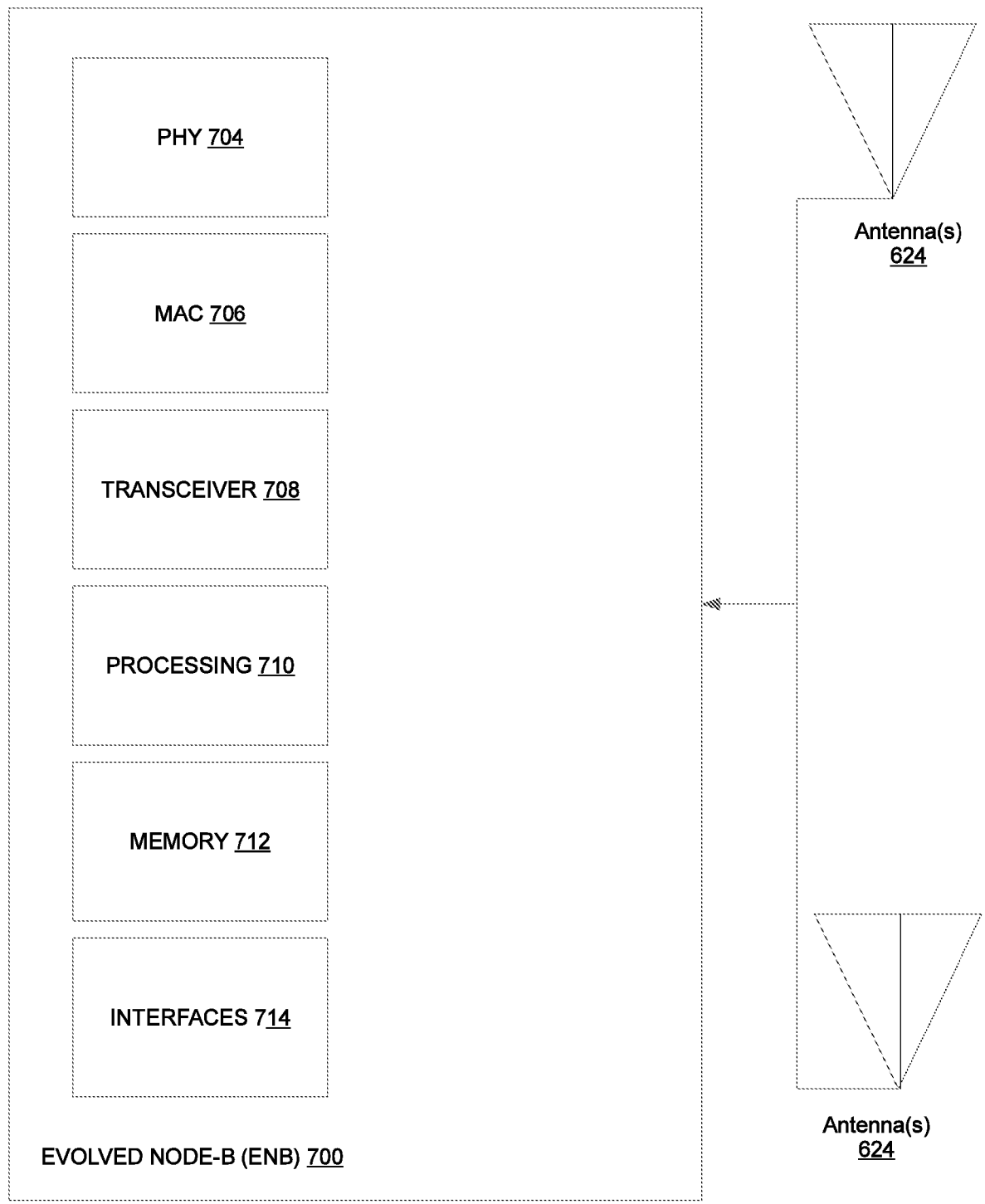
FIG. 7 illustrates a functional diagram of an E-node-B connecting the spectrometer to a network in accordance with some embodiments.

FIG. 7 is a functional diagram of an Evolved Node-B (eNB) in accordance with some embodiments. It should be noted that in some embodiments, the eNB 700 may be a stationary non-mobile device and in others it maybe a device that is in motion. The eNB 700 may be suitable for use as an example eNB 700 as depicted in FIG. 7. The eNB 700 may include physical layer circuitry PHY 704 and a Transceiver 708, one or both of which may enable transmission and reception of signals to and from the spectrometer 600, other eNBs, other mobile devices or other devices using one or more Antenna 624. As an example, the PHY 704 may perform various encoding and decoding functions that may include formation of baseband signals for transmission and decoding of received signals. As another example, the Transceiver 708 may perform various transmission and reception functions such as conversion of signals between a baseband range and a Radio Frequency (RF) range. Accordingly, the PHY 704 and the Transceiver 708 may be separate components or may be part of a combined component. In addition, some of the functionality described may be performed by a combination that may include one, any or all of the PHY 704, the Transceiver 708, and other components or layers. The eNB 700 may also include medium access control layer MAC 706 for controlling access to the wireless medium. The eNB 700 may also include processing circuitry Processing 710 and Memory 712 arranged to perform the operations described herein. The eNB 700 may also include one or more Interfaces 714, which may enable communication with other components, including other eNBs, components in Spectrographic circuitry 615 (FIG. 6) or other network components. In addition, the Interfaces 714 may enable communication with other components that may not be shown in FIG. 7, including components external to the network. The Interfaces 714 may be wired or wireless or a combination thereof.

The Antenna 624 may comprise one or more directional or omnidirectional antennas, including, for example, dipole antennas, monopole antennas, patch antennas, loop antennas, microstrip antennas or other types of antennas suitable for transmission of RF signals. In some multiple-input multiple-output (MIMO) embodiments, the Antenna 624 may be effectively separated to take advantage of spatial diversity and the different channel characteristics that may result.

In some embodiments, the spectrograph 600 or the eNB 700 may be a mobile device and may be a portable wireless communication device, such as a personal digital assistant (PDA), a laptop or portable computer with wireless communication capability, a web tablet, a wireless telephone, a smartphone, a wireless headset, a pager, an instant messaging device, a digital camera, an access point, a television, a wearable device such as a medical device (e.g., a heart rate monitor, a blood pressure monitor, etc.), or other device that may receive and/or transmit information wirelessly. In some embodiments, the spectrometer 600 or eNB 700 may be configured to operate in accordance with 3GPP standards, although the scope of the embodiments is not limited in this respect. Mobile devices or other devices in some embodiments may be configured to operate according to other protocols or standards, including IEEE 802.11 or other IEEE standards. In some embodiments, the spectrometer 600 eNB 700 or other devices may include one or more of a keyboard, a display, a non-volatile memory port, multiple antennas, a graphics processor, an application processor, speakers, and other mobile device elements. The display may be an LCD screen including a touch screen.

SAAS Based Processing of NIR Scans

Figure 8:
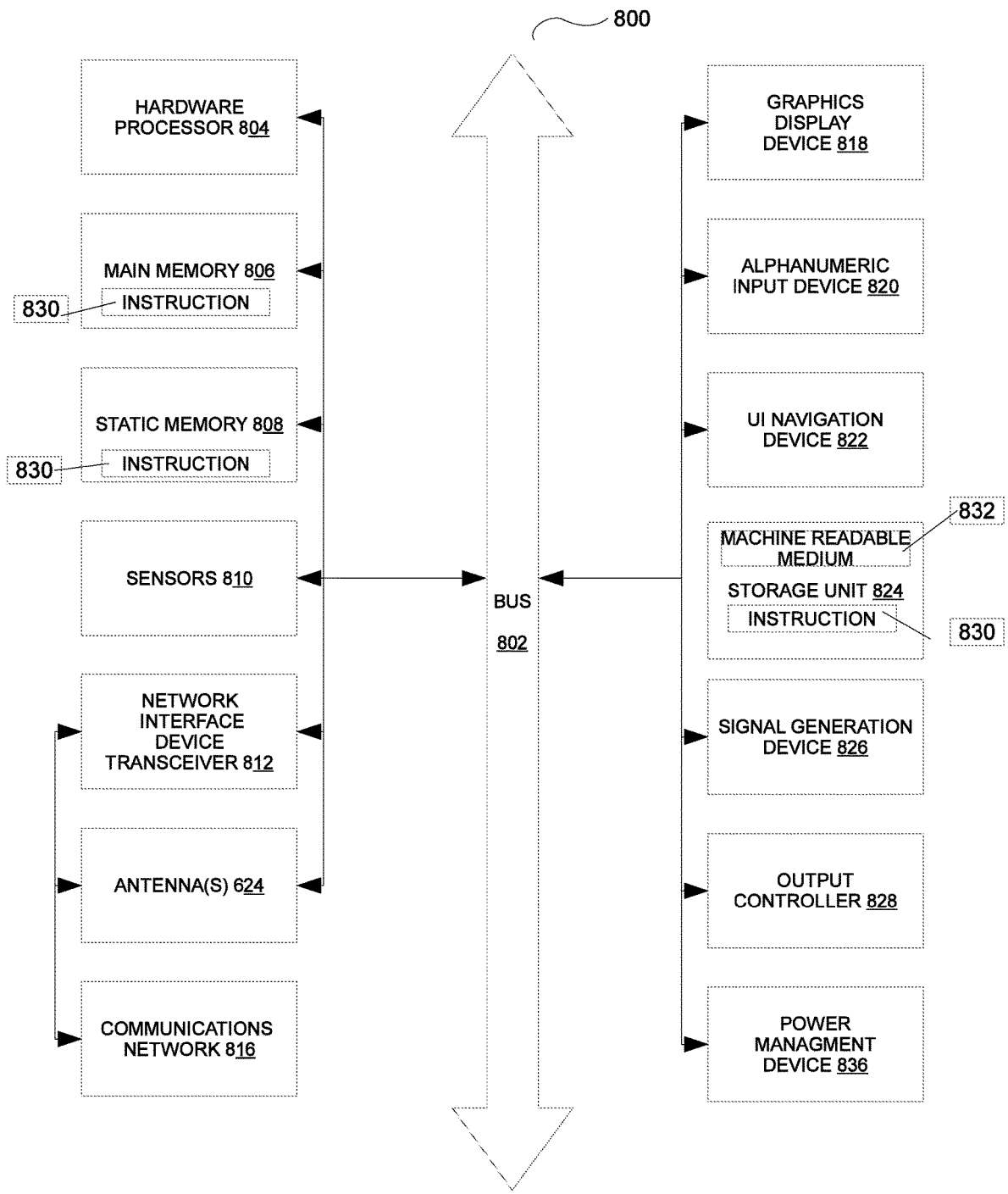
FIG. 8 illustrates example components of the spectrometer and its network connections in accordance with some embodiments.

In FIG. 8, the machine 800 illustrates a block diagram of an example of a spectrometer 600 (FIG. 6) in accordance with some embodiments upon which any one or more of the scanning techniques (e.g., methodologies) discussed herein may be performed. In alternative embodiments, the machine 800 may operate as a standalone device or may be connected (e.g., networked) to other machines. In a networked deployment, the machine 800 may operate in the capacity of a server machine, a client machine, or both in server-client network or in a distributed cloud computing environment. In an example, the machine 800 may act as a peer machine in peer-to-peer (P2P) (or other distributed) network environment. The machine 800 may be a personal computer (PC), a tablet PC, a set-top box (STB), a personal digital assistant (PDA), a mobile telephone, a web appliance, a network router, switch or bridge, or any machine capable of executing instructions (sequential or otherwise) that specify actions to be taken by that machine, such as an eNB 700. Further, while only a single machine is illustrated, the term "machine" shall also be taken to include any collection of machines that individually or jointly execute a set (or multiple sets) of instructions to perform any one or more of the methodologies discussed herein, such as cloud computing, software as a service (SaaS), or other computer cluster configurations.

Examples, as described herein, may include, or may operate on, logic or a number of components, modules, or mechanisms. Modules are tangible entities (e.g., hardware) capable of performing specified operations when operating. A module includes hardware. In an example, the hardware may be specifically configured to carry out a specific operation (e.g., hardwired). In another example, the hardware may include configurable execution units (e.g., transistors, circuits, etc.) and a computer readable medium containing instructions, where the instructions configure the execution units to carry out a specific operation when in operation. The configuring may occur under the direction of the executions units or a loading mechanism. Accordingly, the execution units are communicatively coupled to the computer readable medium when the device is operating. In this example, the execution units may be a member of more than one module. For example, under operation, the execution units may be configured by a first set of instructions to implement a first module at one point in time and reconfigured by a second set of instructions to implement a second module at a second point in time.

The machine (e.g., a special purpose computer system) 800 may include a Hardware Processor 804 (e.g., a central processing unit (CPU), a graphics processing unit (GPU), a hardware processor core, or any combination thereof), a Main Memory 806 and a Static Memory 808, some or all of which may communicate with each other via an interlink (e.g., Bus 802.) The machine 800 may further include a Power Management device 836, a Graphics Display Device 818, an Alphanumeric Input Device 820 (e.g., a keyboard), and a user interface (UI Navigation Device 822 (e.g., a mouse). In an example, the Graphics Display Device 818, Alphanumeric Input Device 820 and UI Navigation Device 822 may be a touch screen display. The machine 800 may additionally include a storage device (i.e., Storage Unit 824), a Signal Generation Device 826 (e.g., a speaker), a Network Interface device/Transceiver 812 coupled to Antenna(s) 624, and one or more Sensor 810, such as a global positioning system (GPS) sensor, compass, accelerometer, or other sensor may be used in conjunction with the Spectrographic circuitry 615 to send signals to the machine 800 The machine 800 may include an Output Controller 828, such as a serial (e.g., universal serial bus (USB), parallel, or other wired or wireless (e.g., infrared (IR), near field communication (NFC), etc.) connection to communicate with or control one or more peripheral devices (e.g., a printer, card reader, etc.)

The Storage Unit 824 may include a Machine-Readable Medium 832 on which is stored one or more sets of data structures or Instructions 830 (e.g., software) embodying or utilized by any one or more of the techniques or functions described herein. The Instructions 830 may also reside, completely or at least partially, within the Main Memory 806, within the Static Memory 808, or within the Hardware Processor 804 during execution thereof by the machine 800. In an example, one or any combination of the Hardware Processor 804, the Main Memory 806, the Static Memory 808, or the Storage Unit 824 may constitute machine readable media.

While the Machine-Readable Medium 832 is illustrated as a single medium, the term "machine readable medium" may include a single medium or multiple medium (e.g., a centralized or distributed database, and/or associated caches and servers) configured to store the one or more Instructions 830.

The term "machine readable medium" may include any medium that is capable of storing, encoding, or carrying instructions for execution by the machine 800 and that cause the machine 800 to perform any one or more of the techniques of the present disclosure, or that is capable of storing, encoding or carrying data structures used by or associated with such instructions.

Non-limiting machine readable medium examples may include solid-state memories, and optical and magnetic media. In an example, a massed machine-readable medium comprises a machine-readable medium with a plurality of particles having resting mass. Specific examples of massed machine-readable media may include: non-volatile memory, such as semiconductor memory devices (e.g., Electrically Programmable Read-Only Memory (EPROM), or Electrically Erasable Programmable Read-Only Memory (EEPROM)) and flash memory devices; magnetic disks, such as internal hard disks and removable disks; magneto-optical disks; and CD-ROM and DVD-ROM disks.

The Instructions 830 may further be transmitted or received over a Communications Network 816 using a transmission medium via the Network Interface device/Transceiver 812 utilizing any one of a number of transfer protocols (e.g., frame relay, internet protocol (IP), transmission control protocol (TCP), user datagram protocol (UDP), hypertext transfer protocol (HTTP), etc.). Example communications networks may include a local area network (LAN), a wide area network (WAN), a packet data network (e.g., the Internet), mobile telephone networks (e.g., cellular networks), Plain Old Telephone (POTS) networks, wireless data networks (e.g., Institute of Electrical and Electronics Engineers (IEEE) 802.11 family of standards known as Wi-Fi®, IEEE 802.16 family of standards known as WiMax®), IEEE 802.15.4 family of standards, and peer-to-peer (P2P) networks, among others. In an example, the Network Interface device/Transceiver 812 may include one or more physical jacks (e.g., Ethernet, coaxial, or phone jacks) or one or more antennas to connect to the Communications Network 816. In an example, the Network Interface device/Transceiver 812 may include a plurality of Antenna(s) 624 to wirelessly communicate using at least one of single-input multiple-output (SIMO), multiple-input multiple-output (MIMO), or multiple-input single-output (MISO) techniques. The term "transmission medium" shall be taken to include any intangible medium that can store, encoding or carrying instructions for execution by the machine 800, and includes digital or analog communications signals or other intangible media to facilitate communication of such software.

Example: Creating a Chemometric Data Set with Market Pigs

Turning to the creation of a scanning chemometric data set, the following example was created by focusing on an aspect of market pigs in the finishing phase (final segment of growing at 115-120 days prior to market) Creating a Chemometric data set requires the use of empirical testing to create an experience-based data set that validates or disproves a working theory on correlation of a scan result v. final results.

Figure 9A:
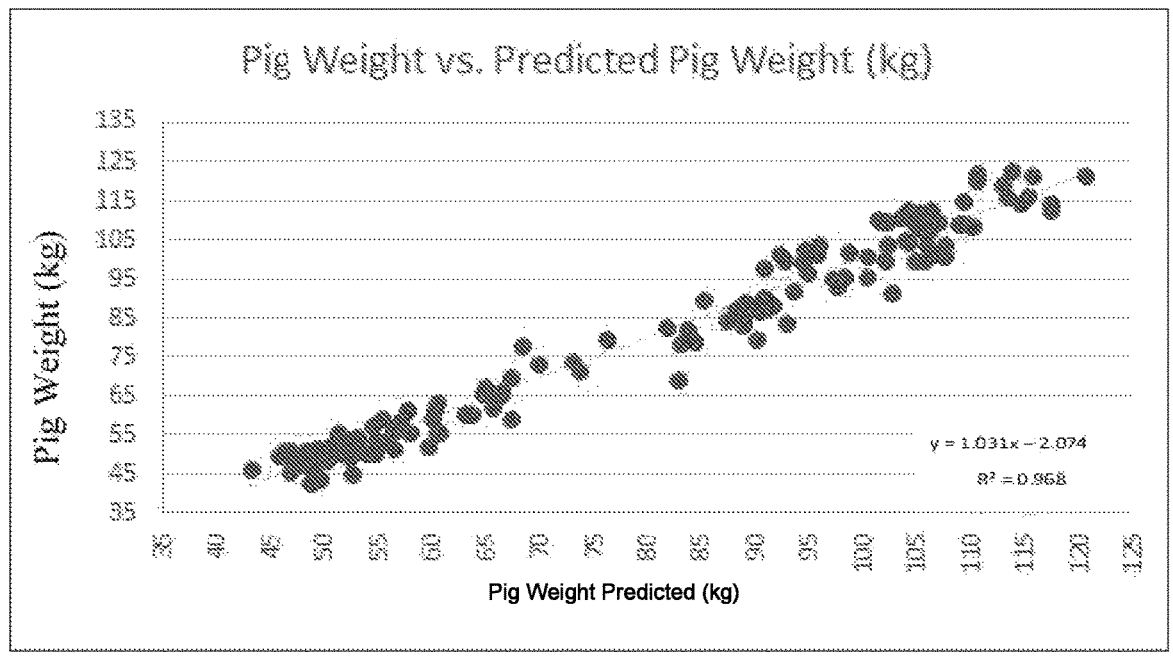
FIG. 9a illustrates examples of a chemometric correlation related to pig weight in accordance with some embodiments.
Figure 9B:
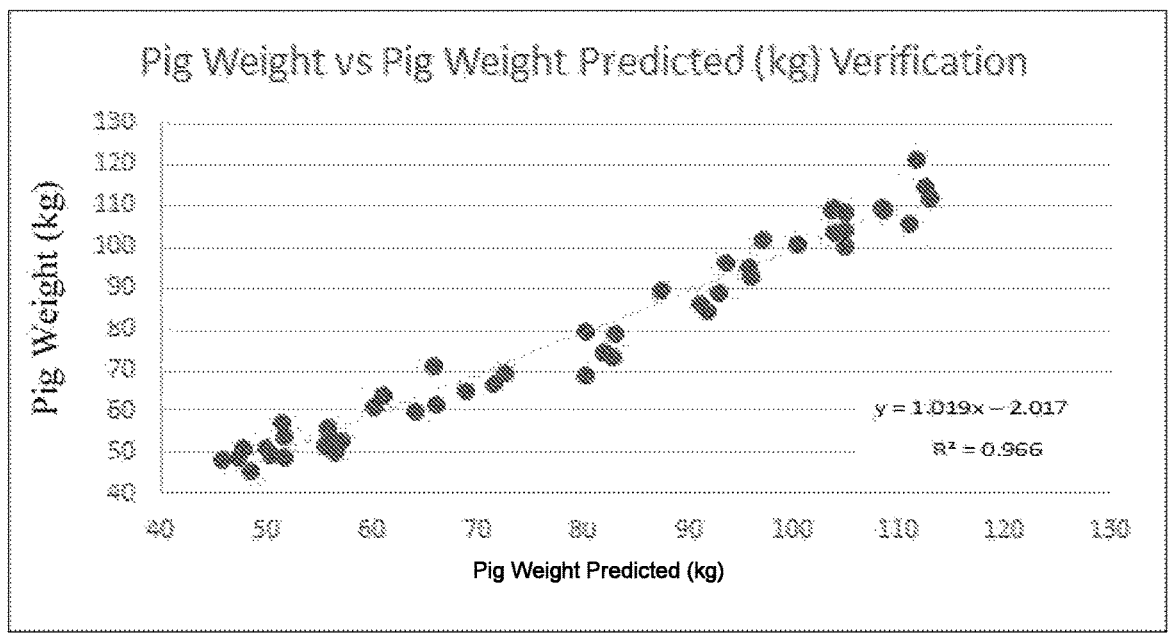
FIG. 9b illustrates examples of a chemometric correlation related to verified pig weight in accordance with some embodiments in accordance with some embodiments.
Figure 10A:
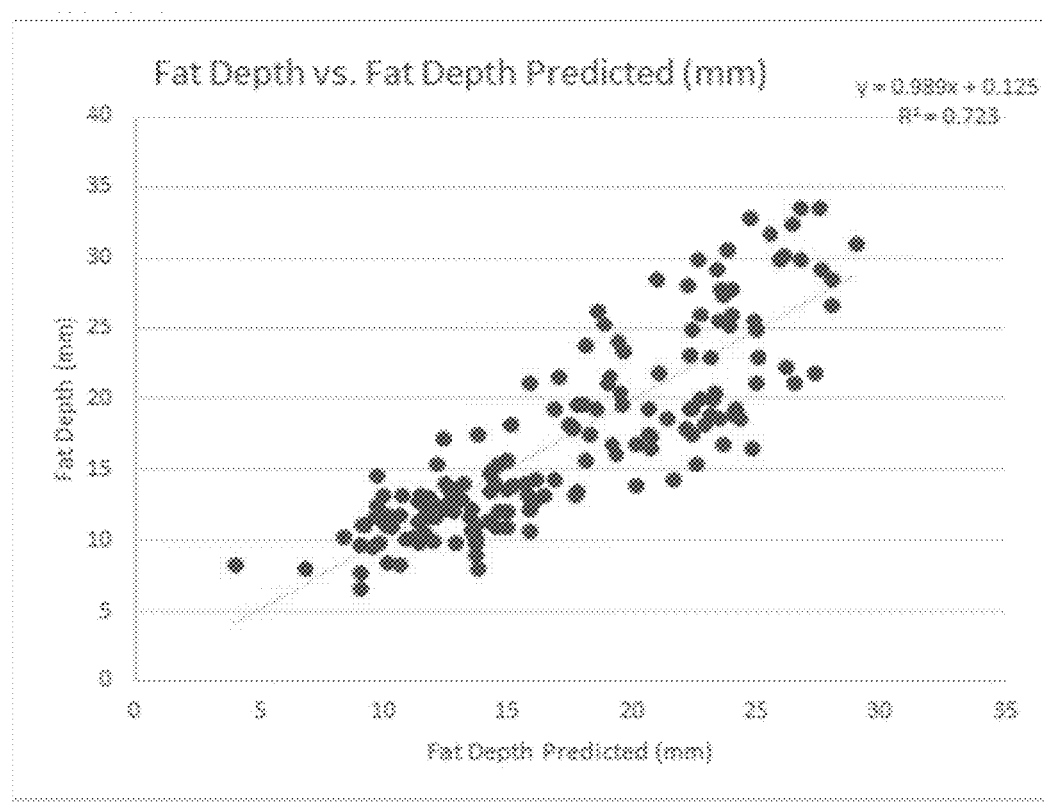
FIG. 10a illustrates examples of a chemometric correlation related to pig fat depth in accordance with some embodiments in accordance with some embodiments.
Figure 10B:
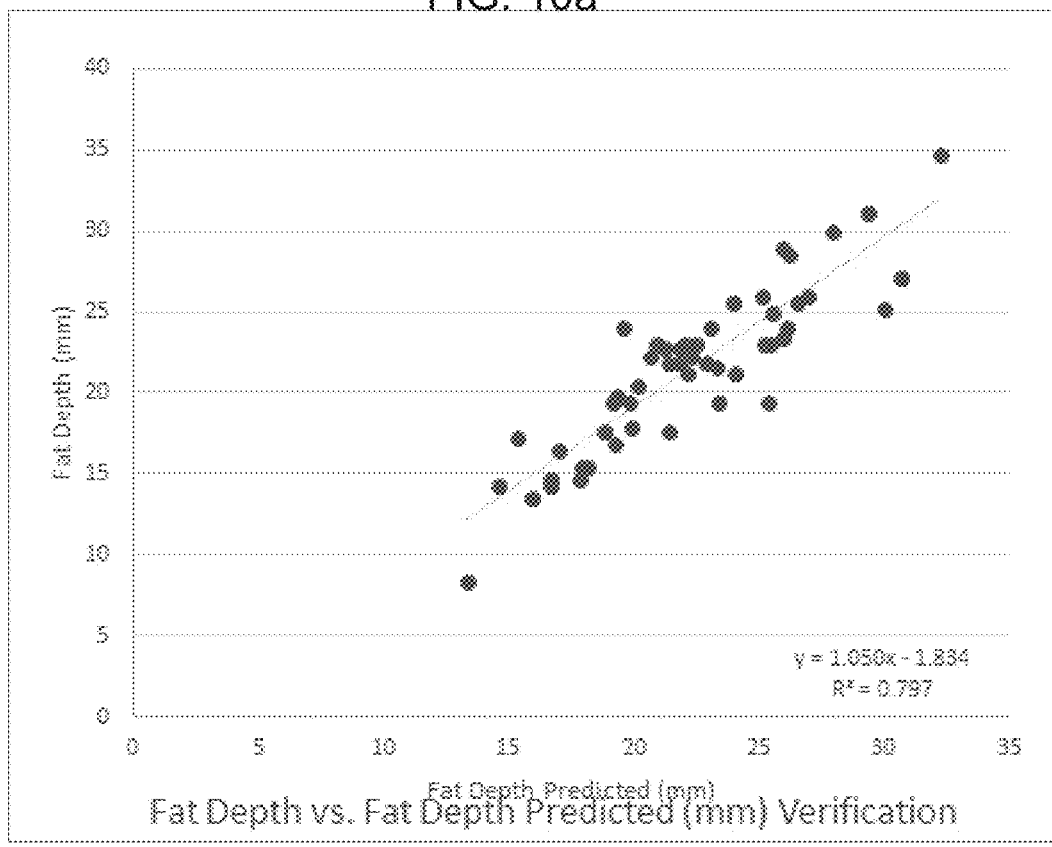
FIG. 10b illustrates examples of a chemometric correlation related to verified pig fat depth in accordance with some embodiments.
Figure 11A:
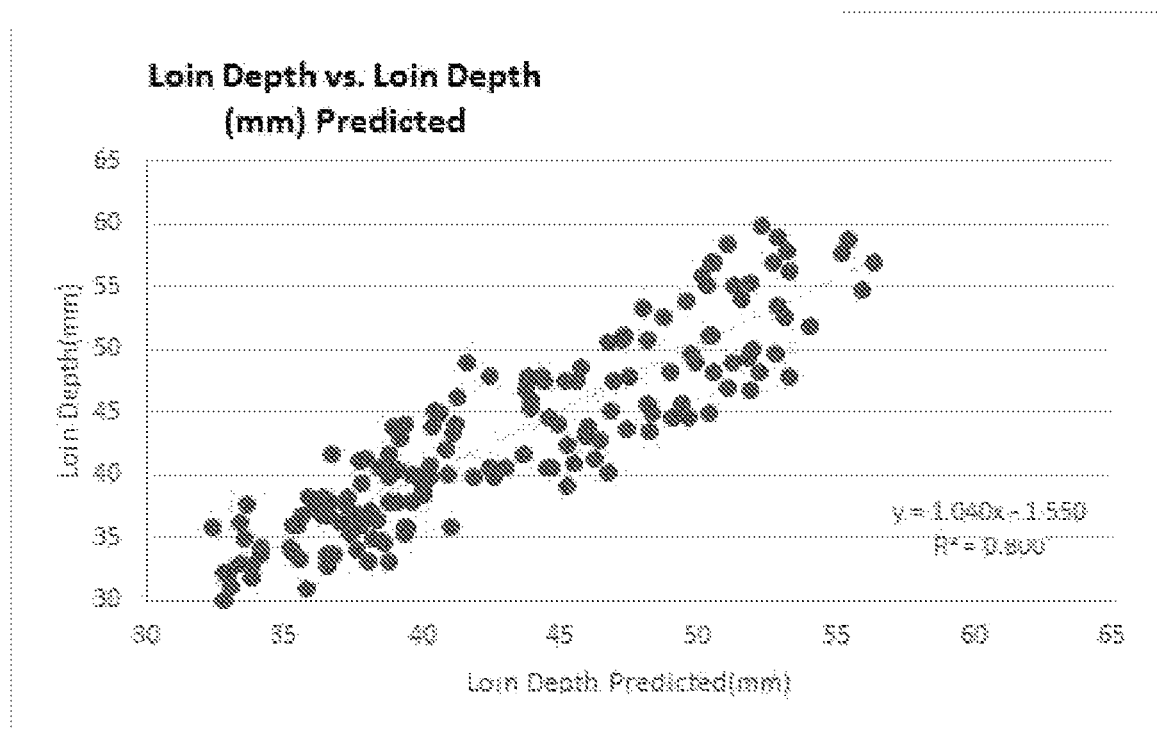
FIG. 11a illustrates examples of a chemometric correlation related to pig loin depth in accordance with some embodiments.
Figure 11B:
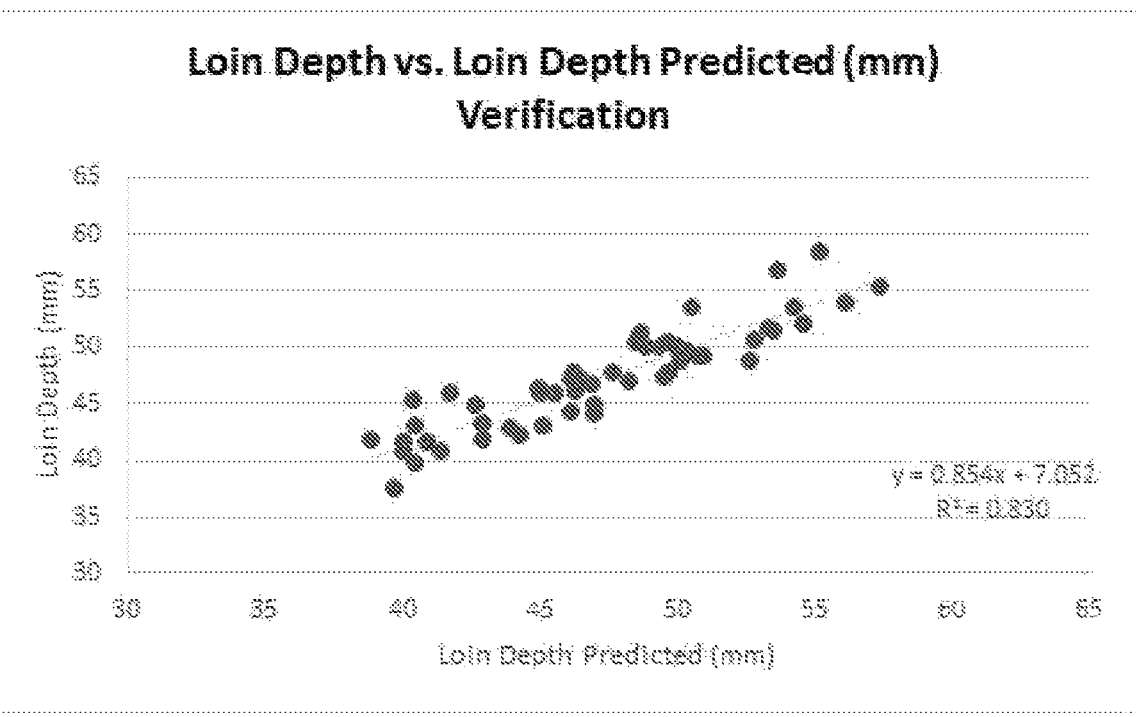
FIG. 11b illustrates examples of a chemometric correlation related to verified pig loin depth in accordance with some embodiments.
Figure 12A:
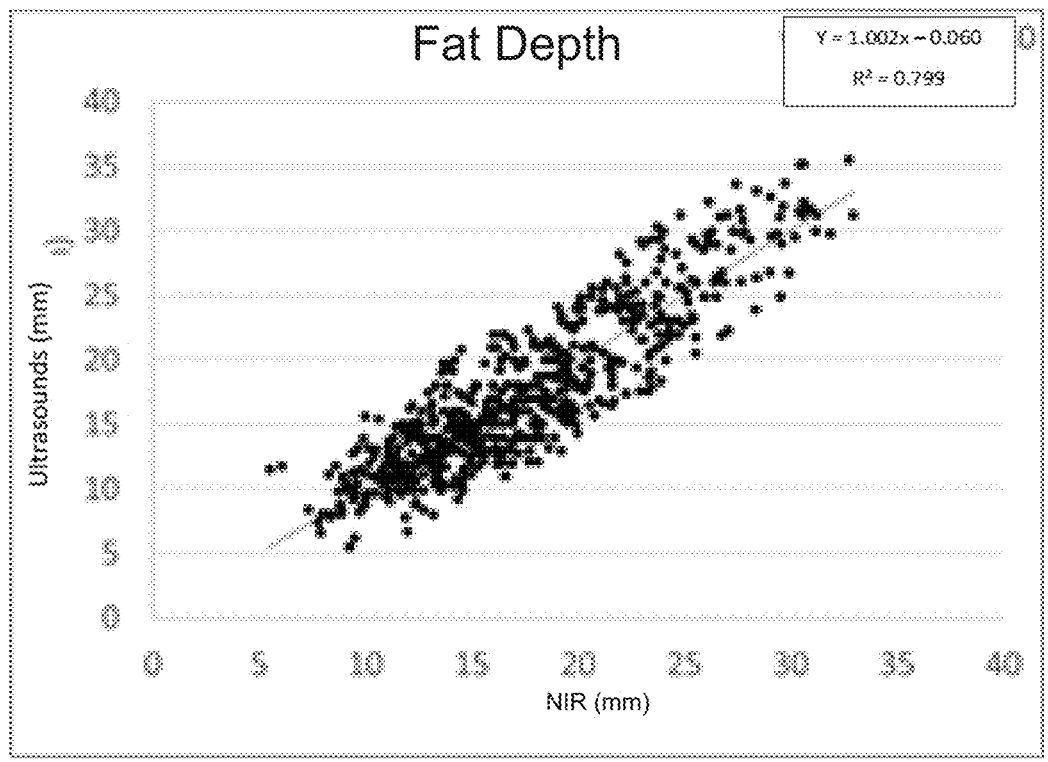
FIG. 12a illustrates examples of a chemometric correlation related to merged correlation of pig fat depth in accordance with some embodiments.
Figure 12B:
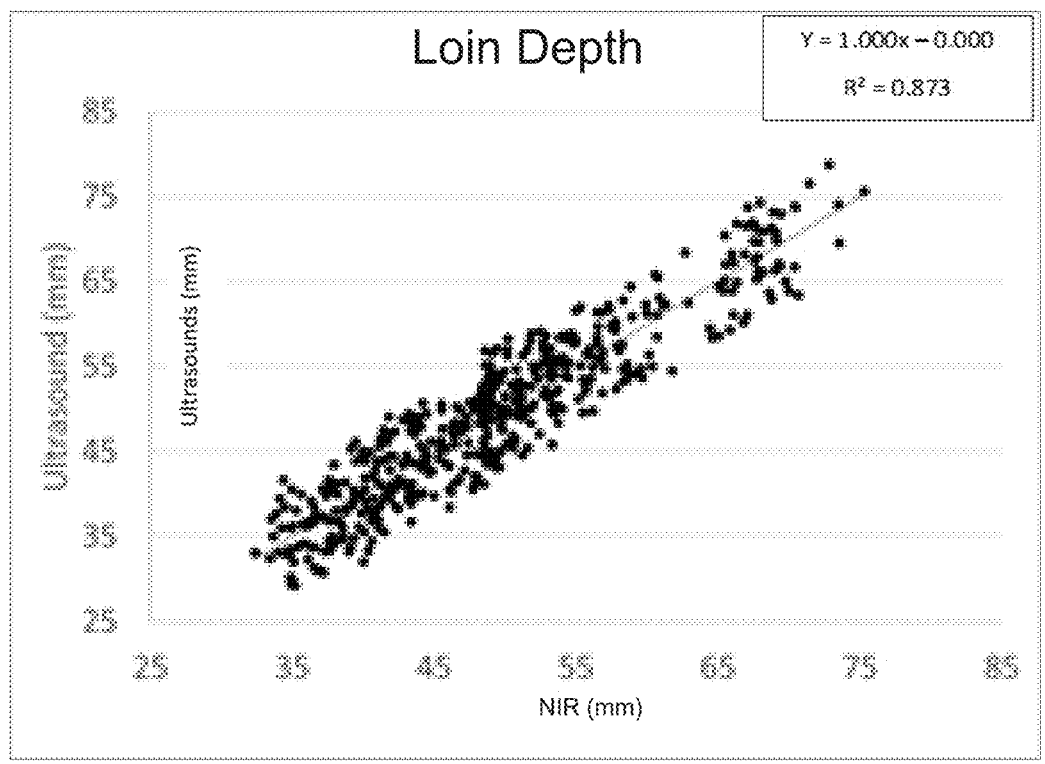
FIG. 12b illustrates examples of a chemometric correlation related to merged pig loin depth in accordance with some embodiments.

In this example of the solution, using a trial of 62 pigs beginning at beginning around 43 kg and ending a final weight of approximately 120 kg. Scanning measurements were taken at 4 intervals during the finisher phase and the actual values were taken posttest or post slaughter. Three separate models are developed to correlate scan values weight estimation, fat depth and loin. The graphs shown in FIG. 9a, 9b, 10a, 10b. 11a, and 11b describe measured outcomes of the models of predictions compared to the actual validated data. In FIG. 9a, the correlation of actual weight of the pigs versus the predicted weight shows the close correlation as well as in FIG. 9b showing the correlation v. ultrasonic prediction. The graph in FIG. 10a shows the model developed to predict Fat Depth in milimeters compared to FIG. 10b, showing the model of measurements taken by the ultrasound. The graphs in FIG. 11a shows the model developed to predict Loin Depth in milimeters compared to FIG. 11b the measurements take by the ultrasound. Finally in FIGS. 12a and 12b respectively, shows the prediction model for predicting loin depth and fat depth from a merged set of 4 trials. This particular model has an error of 3.659 mm in loin depth and an error of 2.795 mm in backfat. This experimental result is on par with ultrasonic measurement.

Example: Creating a Chemometric Data Set with Poultry

Figure 13:
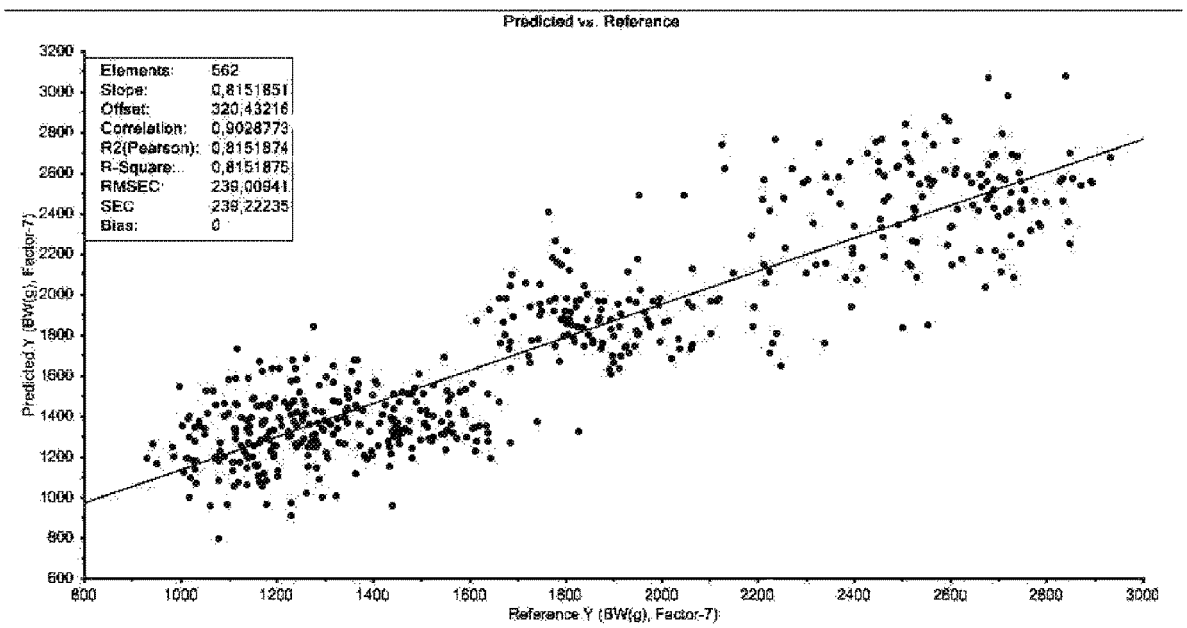
FIG. 13 illustrates examples of a chemometric correlation related to poultry body weight in accordance with some embodiments.
Figure 14:
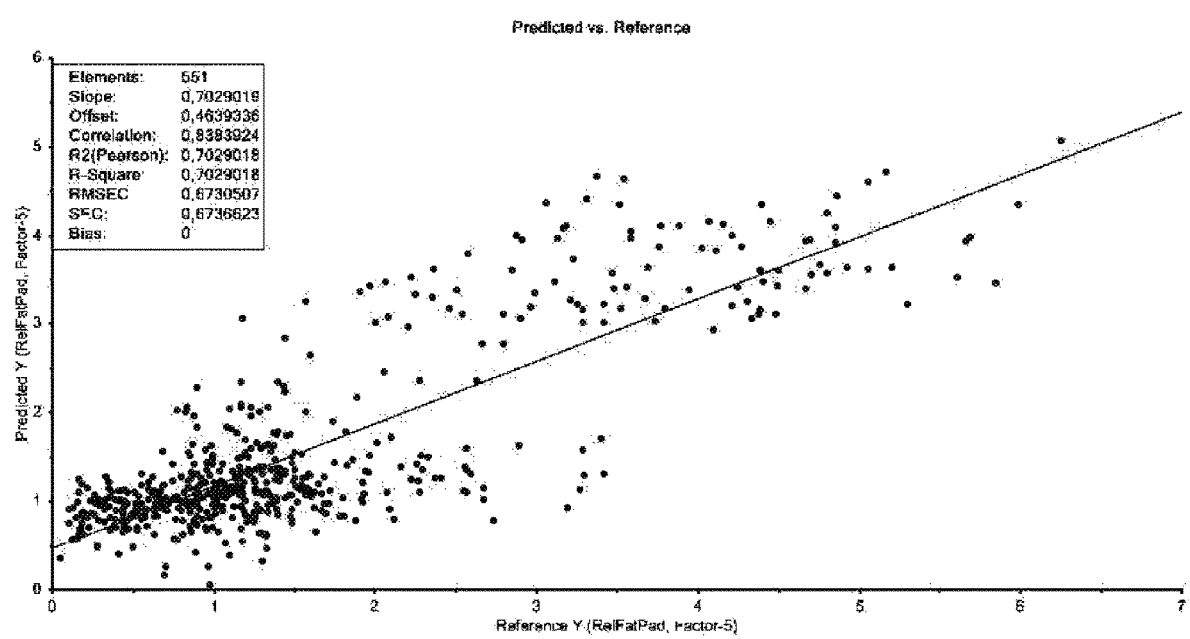
FIG. 14 illustrates examples of a chemometric correlation related to poultry relative fat pad in accordance with some embodiments.
Figure 15:
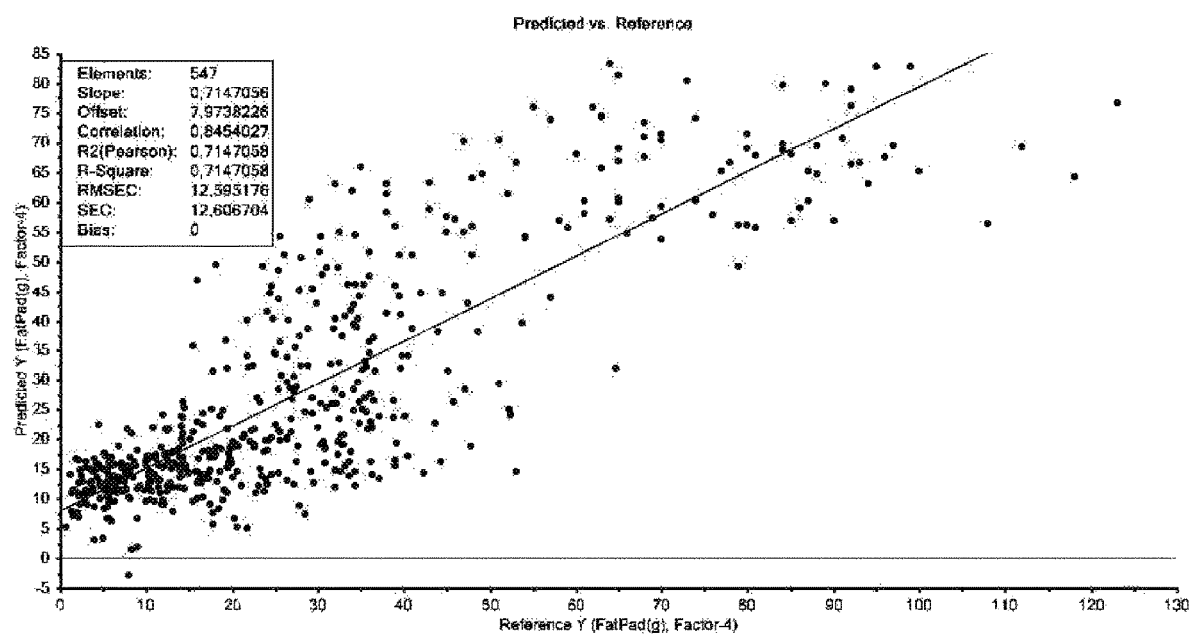
FIG. 15 illustrates examples of a chemometric correlation related to poultry fat pad in accordance with some embodiments.

This example creates and validates models of estimating hen pullet body composition and ingredient digestibility in broiler chickens using a spectrometer scan. Three sample groups were tested comprising 617 chickens roughly 25% broiler composition. Of the total data set, 50 animals were sampled as validation with the remainder used to model the chemometric set of body weight, fat pad models. FIG. 13, 14, 15 shows the model distribution of body weight, relative fat pad and fat pad models respectively.

Validation statistics for the study are presented below.

| VAL | BW(g) | FatPad(g) | Rel.FatPad |
|---|---|---|---|
| Corr | 0.87 | 0.86 | 0.82 |
| SEP | 249 | 11.8 | 0.6 |
| SD | 511 | 23.2 | 1.1 |
| RPDP | 2.1 | 2.0 | 1.8 |

Model statistics for the study are listed below.

| MODEL | BW(g) | FatPad(g) | Rel.FatPad |
|---|---|---|---|
| Corr | 0.90 | 0.84 | 0.84 |
| SEC | 239 | 12.6 | 0.7 |
| SD | 559 | 26.8683 | 1.4 |
| RPDc | 2.3 | 2.1 | 2.0 |

Unless the context clearly requires otherwise, throughout the description and the claims, the words "comprise," "comprising," and the like are to be construed in an inclusive sense as opposed to an exclusive or exhaustive sense; that is to say, in a sense of "including, but not limited to." Words using the singular or plural number also include the plural or singular number respectively. When the claims use the word "or" in reference to a list of two or more items, that word covers all of the following interpretations of the word: any of the items in the list, all of the items in the list, and any combination of the items in the list.

The above detailed descriptions of embodiments of the invention are not intended to be exhaustive or to limit the invention to the precise form disclosed above. Although specific embodiments of, and examples for, the invention are described above for illustrative purposes, various equivalent modifications are possible within the scope of the invention, as those skilled in the relevant art will recognize. For example, while steps are presented in a given order, alternative embodiments may perform steps in a different order. The various embodiments described herein can also be combined to provide further embodiments.

In general, the terms used in the following claims should not be construed to limit the invention to the specific embodiments disclosed in the specification, unless the above detailed description explicitly defines such terms. While certain aspects of the invention are presented below in certain claim forms, the inventors contemplate the various aspects of the invention in any number of claim forms. Accordingly, the inventors reserve the right to add additional claims after filing the application to pursue such additional claim forms for other aspects of the invention.

The invention claimed is:

1. A method comprising:
sensing an emitted spectrum from each animal of a plurality of animals, the plurality of animals comprising one or more aquaculture species, the emitted spectrum associated with a scan proximate a gill area of each animal;
filtering each emitted spectrum to a set of spectral values;
establishing a baseline for the plurality of animals based on the set of spectral values;
correlating the set of spectral values from at least one animal of the plurality of animals to at least one of a set of predetermined chemometric data and the baseline to determine a health metric indicative of a health condition of at least one animal of the plurality of animals, the health metric comprising one or more of a growth rate, a flesh color, and a biomineralization level of the gill area of the at least one animal; and determining a recommendation based on the health metric, wherein the recommendation comprises a change in at least one of a feed, environment, or a medical treatment of the at least one animal.

2. The method of claim 1, wherein the emitted spectrum is associated with a scan from an excreta of the animal.

3. The method of claim 1, wherein the emitted spectrum is associated with scans from an excreta of the animal and at least one other animal.

4. The method of claim 1, wherein the health metric comprises at least one of a weight of the animal or a chemical composition of the animal.

5. The method of claim 1, wherein the emitted spectrum is associated with a scan from at least two discrete areas of the animal.

6. The method of claim 5, wherein the at least two discrete areas comprise a primary scan area and a secondary scan area.

7. The method of claim 1, wherein the emitted spectrum is indicative of at least one of an estimated weight, fat depth, loin depth, fat content, chemical pigment, nutritional content, or coloration of the animal.

8. The method of claim 1, wherein the set of predetermined chemometric data comprises data related to at least one of a body weight, body composition, fat depth, loin depth, or animal serum protein level.

9. The method of claim 1, wherein the animal is at least one of a meat producing animal, an egg producing animal, a hide bearing animal, a milk producing animal, an oil producing animal, or a pharmaceutical producing animal.

10. The method of claim 1, wherein the correlation of the set of spectral values with the set of predetermined chemometric data further determines at least one of an estimated final market state of the animal or an environmental condition of the animal.

11. The method of claim 1, further comprising transmitting the recommendation to a sensor unit.

12. The method of claim 1, wherein the emitted spectrum is associated with a first scan from an excreta of the animal and a second scan from at least one discrete area of the animal.

13. The method of claim 1, wherein sensing the emitted spectrum from each animal of the plurality of animals comprises sensing a near-infrared emitted spectrum from each animal of the plurality of animals.

14. The method of claim 1, wherein the emitted spectrum has a wavelength in a range from 780 nm to 2500 nm.

15. The method of claim 1, wherein the animal is an aquaculture species.

16. The method of claim 15, wherein the aquaculture species comprises one or more of salmonid, crustacea, amphibious species, reptilian species, and finfish species.

17. The method of claim 1, wherein the health metric comprises the growth rate of the gill area of the at least one animal.

18. The method of claim 1, wherein the health metric comprises the flesh color of the gill area of the at least one animal.

19. The method of claim 1, wherein the health metric comprises the bio-mineralization level of one or both of a shell or scale of the gill area of the at least one animal.

20. The method of claim 1, further comprising:
determining a water quality that is optimized for the at least one animal based on the health metric; and
determining a recommendation based on the health metric and the water quality.

21. A non-transitory computer-readable media comprising computer-readable instructions stored thereon that when executed by a processor cause the processor to:
receive a set of spectral values from a sensor unit that detects an emitted spectrum from each animal of a plurality of animals and filters each emitted spectrum to the set of spectral values, the plurality of animals comprising one or more aquaculture species, the emitted spectrum associated with a scan proximate a gill area of each animal;
establish a baseline for the plurality of animals based on the received set of spectral values;
correlate the set of spectral values from at least one animal of the plurality of animals to at least one of a set of predetermined chemometric data and the baseline to determine a health metric indicative of a health condition of at least one animal of the plurality of animals, the health metric comprising one or more of a growth metric, a flesh color, and a biomineralization level of the gill area of the at least one animal; and
determine a recommendation based on the health metric, wherein the recommendation comprises a change in at least one of a feed, environment, or a medical treatment of the at least one animal.

22. The non-transitory computer-readable media of claim 21, wherein the change in the feed comprises a change in at least one of a feed formulation or an amount of feed.

23. The non-transitory computer-readable media of claim 21, wherein the recommendation further comprises at least one of a watering recommendation or a supplementation recommendation.

24. The non-transitory computer-readable media of claim 21, wherein the recommendation further comprises at least one of a segregation recommendation or a culling recommendation.

25. The non-transitory computer-readable media of claim 21, wherein the health metric comprises at least one of a weight of the animal or a chemical composition of the animal.

26. The non-transitory computer-readable media of claim 21, wherein the emitted spectrum is associated with a scan from at least two discrete areas of the animal, and wherein the at least two discrete areas comprise a primary scan area and a secondary scan area.

27. The non-transitory computer-readable media of claim 21, wherein the emitted spectrum is indicative of at least one of an estimated weight, fat depth, loin depth, fat content, chemical pigment, or nutritional content or coloration of the animal.

28. The non-transitory computer-readable media of claim 21, wherein the animal is at least one of a meat producing animal, an egg producing animal, a hide bearing animal, a milk producing animal, an oil producing animal or a pharmaceutical producing animal.

* * * * *